US008353949B2

(12) United States Patent  (10) Patent No.: US 8,353,949 B2
Weber et al.                (45) Date of Patent:     Jan. 15, 2013

(54) MEDICAL DEVICES WITH DRUG-ELUTING COATING

(75) Inventors: Jan Weber, Maastricht (NL); Matthew Miller, Stillwater, MN (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 1303 days.

(21) Appl. No.: 11/852,475

(22) Filed: Sep. 10, 2007

(65) Prior Publication Data

US 2008/0071355 A1    Mar. 20, 2008

Related U.S. Application Data

(60) Provisional application No. 60/844,471, filed on Sep. 14, 2006.

(51) Int. Cl.
*A61F 2/06* (2006.01)
*A61L 33/00* (2006.01)
*B05D 3/00* (2006.01)

(52) U.S. Cl. .................. 623/1.15; 623/1.46; 427/2.25

(58) Field of Classification Search .......... 623/1.1, 623/1.12, 1.15–1.2, 1.39, 1.42–1.46; 427/2.1, 427/2.4, 2.5
See application file for complete search history.

(56) References Cited

U.S. PATENT DOCUMENTS

| 3,751,283 A | 8/1973 | Dawson |
| 3,758,396 A | 9/1973 | Vieth et al. |
| 3,910,819 A | 10/1975 | Rembaum et al. |
| 3,948,254 A | 4/1976 | Zaffaroni |
| 3,952,334 A | 4/1976 | Bokros et al. |
| 3,970,445 A | 7/1976 | Gale et al. |
| 3,993,072 A | 11/1976 | Zaffaroni |
| 4,044,404 A | 8/1977 | Martin et al. |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,309,996 A | 1/1982 | Theeuwes |
| 4,321,311 A | 3/1982 | Strangman |
| 4,330,891 A | 5/1982 | Branemark et al. |
| 4,334,327 A | 6/1982 | Lyman et al. |

(Continued)

FOREIGN PATENT DOCUMENTS

AT    232704    3/2003

(Continued)

OTHER PUBLICATIONS

U.S. Appl. No. 11/763,770, Weber et al.

(Continued)

*Primary Examiner* — Gary Jackson
*Assistant Examiner* — Michael Mendoza
(74) *Attorney, Agent, or Firm* — Fish & Richardson P.C.

(57) ABSTRACT

Medical devices, such as endoprostheses, and methods of making the devices are described. In one embodiment, a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure is described. One or more wall surfaces of the tubular structure can bear a coating whose selected regions define at least one depression. The coating can further include at least one biologically active substance.

34 Claims, 7 Drawing Sheets

U.S. PATENT DOCUMENTS

| | | |
|---|---|---|
| 4,401,546 A | 8/1983 | Nakamura et al. |
| 4,407,695 A | 10/1983 | Deckman et al. |
| 4,475,972 A | 10/1984 | Wong |
| 4,565,744 A | 1/1986 | Walter et al. |
| 4,585,652 A | 4/1986 | Miller et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,733,665 A | 3/1988 | Palmaz |
| 4,738,740 A | 4/1988 | Pinchuk et al. |
| 4,743,252 A | 5/1988 | Martin et al. |
| 4,784,659 A | 11/1988 | Fleckenstein et al. |
| 4,800,882 A | 1/1989 | Gianturco |
| 4,842,505 A | 6/1989 | Annis et al. |
| 4,886,062 A | 12/1989 | Wiktor |
| 4,902,290 A | 2/1990 | Fleckenstein et al. |
| 4,954,126 A | 9/1990 | Wallsten |
| 4,976,692 A | 12/1990 | Atad |
| 4,994,071 A | 2/1991 | MacGregor |
| 5,061,275 A | 10/1991 | Wallsten et al. |
| 5,061,914 A | 10/1991 | Busch et al. |
| 5,073,365 A | 12/1991 | Katz et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,171,607 A | 12/1992 | Cumbo |
| 5,195,969 A | 3/1993 | Wang et al. |
| 5,205,921 A | 4/1993 | Shirkanzadeh |
| 5,219,611 A | 6/1993 | Giannelis et al. |
| 5,232,444 A | 8/1993 | Just et al. |
| 5,236,413 A | 8/1993 | Feiring |
| 5,242,706 A | 9/1993 | Cotell et al. |
| 5,250,242 A | 10/1993 | Nishio et al. |
| 5,270,086 A | 12/1993 | Hamlin |
| 5,279,292 A | 1/1994 | Baumann et al. |
| 5,290,585 A | 3/1994 | Elton |
| 5,302,414 A | 4/1994 | Alkhimov et al. |
| 5,304,121 A | 4/1994 | Sahatjian |
| 5,314,453 A | 5/1994 | Jeutter |
| 5,322,520 A | 6/1994 | Milder |
| 5,326,354 A | 7/1994 | Kwarteng |
| 5,348,553 A | 9/1994 | Whitney |
| 5,366,504 A | 11/1994 | Andersen et al. |
| 5,368,881 A | 11/1994 | Kelman et al. |
| 5,378,146 A | 1/1995 | Sterrett |
| 5,380,298 A | 1/1995 | Zabetakis et al. |
| 5,383,935 A | 1/1995 | Shirkhanzadeh |
| 5,397,307 A | 3/1995 | Goodin |
| 5,405,367 A | 4/1995 | Schulman et al. |
| 5,439,446 A | 8/1995 | Barry |
| 5,443,496 A | 8/1995 | Schwartz et al. |
| 5,447,724 A | 9/1995 | Helmus et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,545,208 A | 8/1996 | Wolff et al. |
| 5,551,954 A | 9/1996 | Buscemi et al. |
| 5,569,463 A | 10/1996 | Helmus et al. |
| 5,578,075 A | 11/1996 | Dayton |
| 5,587,507 A | 12/1996 | Kohn et al. |
| 5,591,224 A | 1/1997 | Schwartz et al. |
| 5,603,556 A | 2/1997 | Klink |
| 5,605,696 A | 2/1997 | Eury et al. |
| 5,607,463 A | 3/1997 | Schwartz et al. |
| 5,607,467 A | 3/1997 | Froix |
| 5,609,629 A | 3/1997 | Fearnot et al. |
| 5,614,549 A | 3/1997 | Greenwald et al. |
| 5,624,411 A | 4/1997 | Tuch |
| 5,649,951 A | 7/1997 | Davidson |
| 5,649,977 A | 7/1997 | Campbell |
| 5,672,242 A | 9/1997 | Jen |
| 5,674,192 A | 10/1997 | Sahatjian et al. |
| 5,674,242 A | 10/1997 | Phan et al. |
| 5,679,440 A | 10/1997 | Kubota |
| 5,681,196 A | 10/1997 | Jin et al. |
| 5,690,670 A | 11/1997 | Davidson |
| 5,693,085 A | 12/1997 | Buirge et al. |
| 5,693,928 A | 12/1997 | Egitto et al. |
| 5,711,866 A | 1/1998 | Lashmore et al. |
| 5,733,924 A | 3/1998 | Kanda et al. |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,758,562 A | 6/1998 | Thompson |
| 5,761,775 A | 6/1998 | Legome et al. |
| 5,769,883 A | 6/1998 | Buscemi et al. |
| 5,772,864 A | 6/1998 | Moller et al. |
| 5,776,184 A | 7/1998 | Tuch |
| 5,780,807 A | 7/1998 | Saunders |
| 5,788,687 A | 8/1998 | Batich et al. |
| 5,788,979 A | 8/1998 | Alt et al. |
| 5,795,626 A | 8/1998 | Gabel et al. |
| 5,797,898 A | 8/1998 | Santini, Jr. et al. |
| 5,807,407 A | 9/1998 | England et al. |
| 5,817,046 A | 10/1998 | Glickman |
| 5,824,045 A | 10/1998 | Alt |
| 5,824,048 A | 10/1998 | Tuch |
| 5,824,049 A | 10/1998 | Ragheb et al. |
| 5,824,077 A | 10/1998 | Mayer |
| 5,830,480 A | 11/1998 | Ducheyne et al. |
| 5,837,313 A | 11/1998 | Ding et al. |
| 5,843,089 A | 12/1998 | Sahatjian et al. |
| 5,843,172 A | 12/1998 | Yan |
| 5,852,088 A | 12/1998 | Dismukes et al. |
| 5,858,556 A | 1/1999 | Eckert et al. |
| 5,873,904 A | 2/1999 | Ragheb et al. |
| 5,874,134 A | 2/1999 | Rao et al. |
| 5,879,697 A | 3/1999 | Ding et al. |
| 5,882,335 A | 3/1999 | Leone et al. |
| 5,888,591 A | 3/1999 | Gleason et al. |
| 5,891,108 A | 4/1999 | Leone et al. |
| 5,891,192 A | 4/1999 | Murayama et al. |
| 5,902,266 A | 5/1999 | Leone et al. |
| 5,922,021 A | 7/1999 | Jang |
| 5,928,247 A | 7/1999 | Barry et al. |
| 5,951,881 A | 9/1999 | Rogers et al. |
| 5,954,706 A | 9/1999 | Sahatjian |
| 5,962,136 A | 10/1999 | Dewez et al. |
| 5,968,091 A | 10/1999 | Pinchuk et al. |
| 5,968,092 A | 10/1999 | Buscemi et al. |
| 5,968,640 A | 10/1999 | Lubowitz et al. |
| 5,972,027 A | 10/1999 | Johnson |
| 5,977,204 A | 11/1999 | Boyan et al. |
| 5,980,551 A | 11/1999 | Summers et al. |
| 5,980,564 A | 11/1999 | Stinson |
| 5,980,566 A | 11/1999 | Alt et al. |
| 6,013,591 A | 1/2000 | Ying et al. |
| 6,017,577 A | 1/2000 | Hostettler et al. |
| 6,022,812 A | 2/2000 | Smith et al. |
| 6,025,036 A | 2/2000 | McGill et al. |
| 6,034,295 A | 3/2000 | Rehberg et al. |
| 6,045,877 A | 4/2000 | Gleason et al. |
| 6,063,101 A | 5/2000 | Jacobsen et al. |
| 6,071,305 A | 6/2000 | Brown et al. |
| 6,074,135 A | 6/2000 | Tapphorn et al. |
| 6,096,070 A | 8/2000 | Ragheb et al. |
| 6,099,561 A | 8/2000 | Alt |
| 6,099,562 A | 8/2000 | Ding et al. |
| 6,106,473 A | 8/2000 | Violante et al. |
| 6,110,204 A | 8/2000 | Lazarov et al. |
| 6,120,536 A | 9/2000 | Ding et al. |
| 6,120,660 A | 9/2000 | Chu et al. |
| 6,122,564 A | 9/2000 | Koch et al. |
| 6,139,573 A | 10/2000 | Sogard et al. |
| 6,139,913 A | 10/2000 | Van Steenkiste et al. |
| 6,153,252 A | 11/2000 | Hossainy et al. |
| 6,156,435 A | 12/2000 | Gleason et al. |
| 6,159,142 A | 12/2000 | Alt |

| | | |
|---|---|---|
| 6,171,609 B1 | 1/2001 | Kunz |
| 6,174,329 B1 | 1/2001 | Callol et al. |
| 6,174,330 B1 | 1/2001 | Stinson |
| 6,180,184 B1 | 1/2001 | Gray et al. |
| 6,187,037 B1 | 2/2001 | Satz |
| 6,190,404 B1 | 2/2001 | Palmaz et al. |
| 6,193,761 B1 | 2/2001 | Treacy |
| 6,200,685 B1 | 3/2001 | Davidson |
| 6,203,536 B1 | 3/2001 | Berg et al. |
| 6,206,915 B1 | 3/2001 | Fagan et al. |
| 6,206,916 B1 | 3/2001 | Furst |
| 6,210,715 B1 | 4/2001 | Starling et al. |
| 6,212,434 B1 | 4/2001 | Scheiner et al. |
| 6,214,042 B1 | 4/2001 | Jacobsen et al. |
| 6,217,607 B1 | 4/2001 | Alt |
| 6,231,600 B1 | 5/2001 | Zhong |
| 6,240,616 B1 | 6/2001 | Yan |
| 6,241,762 B1 | 6/2001 | Shanley |
| 6,245,104 B1 | 6/2001 | Alt |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 * | 8/2001 | Wright et al. ............... 623/1.42 |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 | 3/2002 | Starling et al. |
| 6,358,556 B1 | 3/2002 | Ding et al. |
| 6,361,780 B1 | 3/2002 | Ley et al. |
| 6,364,856 B1 | 4/2002 | Ding et al. |
| 6,365,222 B1 | 4/2002 | Wagner et al. |
| 6,367,412 B1 | 4/2002 | Ramaswamy et al. |
| 6,368,658 B1 | 4/2002 | Schwarz et al. |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Bulrge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 | 7/2002 | Yang et al. |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 | 11/2002 | Li et al. |
| 6,488,715 B1 | 12/2002 | Pope et al. |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B1 | 2/2003 | DiMatteo et al. |
| 6,514,289 B1 | 2/2003 | Pope et al. |
| 6,517,888 B1 | 2/2003 | Weber |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 | 3/2003 | Bates et al. |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,585,765 B1 | 7/2003 | Hossainy et al. |
| 6,599,558 B1 | 7/2003 | Al-Lamee et al. |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Castro et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,656,506 B1 | 12/2003 | Wu et al. |
| 6,660,034 B1 | 12/2003 | Mandrusov et al. |
| 6,660,343 B2 | 12/2003 | McGill et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 | 10/2004 | Wu et al. |

| | | | | | | |
|---|---|---|---|---|---|---|
| 6,807,440 B2 | 10/2004 | Weber | | 7,235,098 B2 | 6/2007 | Palmaz |
| 6,815,609 B1 | 11/2004 | Wang et al. | | 7,238,199 B2 | 7/2007 | Feldman et al. |
| 6,820,676 B2 | 11/2004 | Palmaz et al. | | 7,244,272 B2 | 7/2007 | Dubson et al. |
| 6,827,737 B2 | 12/2004 | Hill et al. | | 7,247,166 B2 | 7/2007 | Pienknagura |
| 6,830,598 B1 | 12/2004 | Sung | | 7,247,338 B2 | 7/2007 | Pui et al. |
| 6,833,004 B2 | 12/2004 | Ishii et al. | | 7,261,735 B2 | 8/2007 | Llanos et al. |
| 6,846,323 B2 | 1/2005 | Yip et al. | | 7,261,752 B2 | 8/2007 | Sung |
| 6,846,841 B2 | 1/2005 | Hunter et al. | | 7,273,493 B2 | 9/2007 | Ledergerber |
| 6,849,085 B2 | 2/2005 | Marton | | 7,294,409 B2 | 11/2007 | Lye et al. |
| 6,849,089 B2 | 2/2005 | Stoll | | 7,311,727 B2 | 12/2007 | Mazumder et al. |
| 6,852,122 B2 | 2/2005 | Rush | | 7,329,431 B2 | 2/2008 | Ishii |
| 6,858,221 B2 | 2/2005 | Sirhan et al. | | 7,344,563 B2 | 3/2008 | Vallana et al. |
| 6,861,088 B2 | 3/2005 | Weber et al. | | 7,368,065 B2 | 5/2008 | Yang et al. |
| 6,866,805 B2 | 3/2005 | Hong et al. | | 7,393,589 B2 | 7/2008 | Aharonov et al. |
| 6,869,443 B2 | 3/2005 | Buscemi et al. | | 7,396,538 B2 | 7/2008 | Granada et al. |
| 6,869,701 B1 | 3/2005 | Aita et al. | | 7,402,173 B2 | 7/2008 | Scheuermann et al. |
| 6,875,227 B2 | 4/2005 | Yoon | | 7,416,558 B2 | 8/2008 | Yip et al. |
| 6,878,249 B2 | 4/2005 | Kouyama et al. | | 7,435,256 B2 | 10/2008 | Stenzel |
| 6,884,429 B2 | 4/2005 | Koziak et al. | | 7,482,034 B2 | 1/2009 | Boulais |
| 6,896,697 B1 | 5/2005 | Yip et al. | | 7,494,950 B2 | 2/2009 | Armitage et al. |
| 6,899,914 B2 | 5/2005 | Schaldach et al. | | 7,497,876 B2 | 3/2009 | Tuke et al. |
| 6,904,658 B2 | 6/2005 | Hines | | 7,547,445 B2 | 6/2009 | Chudzik et al. |
| 6,908,622 B2 | 6/2005 | Barry et al. | | 7,563,324 B1 | 7/2009 | Chen et al. |
| 6,908,624 B2 | 6/2005 | Hossainy et al. | | 7,575,593 B2 | 8/2009 | Rea et al. |
| 6,913,617 B1 | 7/2005 | Reiss | | 7,575,632 B2 | 8/2009 | Sundar |
| 6,915,796 B2 | 7/2005 | Sung | | 7,635,515 B1 | 12/2009 | Sherman |
| 6,918,927 B2 | 7/2005 | Bates et al. | | 7,638,156 B1 | 12/2009 | Hossainy et al. |
| 6,918,929 B2 | 7/2005 | Udipi et al. | | 7,643,885 B2 * | 1/2010 | Maschke ...................... 607/120 |
| 6,923,829 B2 | 8/2005 | Boyle et al. | | 7,691,461 B1 | 4/2010 | Prabhu |
| 6,924,004 B2 | 8/2005 | Rao et al. | | 7,713,297 B2 | 5/2010 | Alt |
| 6,932,930 B2 | 8/2005 | DeSimone et al. | | 7,727,275 B2 | 6/2010 | Betts et al. |
| 6,936,066 B2 | 8/2005 | Palmaz et al. | | 7,744,644 B2 * | 6/2010 | Weber et al. ................. 623/1.42 |
| 6,939,320 B2 | 9/2005 | Lennox | | 7,749,264 B2 | 7/2010 | Gregorich et al. |
| 6,951,053 B2 | 10/2005 | Padilla et al. | | 7,758,636 B2 | 7/2010 | Shanley et al. |
| 6,953,560 B1 | 10/2005 | Castro et al. | | 7,771,773 B2 | 8/2010 | Namavar |
| 6,955,661 B1 | 10/2005 | Herweck et al. | | 7,785,653 B2 | 8/2010 | Shanley et al. |
| 6,955,685 B2 | 10/2005 | Escamilla et al. | | 7,837,726 B2 | 11/2010 | Von Oepen et al. |
| 6,962,822 B2 | 11/2005 | Hart et al. | | 7,901,452 B2 | 3/2011 | Gale et al. |
| 6,971,813 B2 * | 12/2005 | Shekalim et al. ............. 401/208 | | 7,914,809 B2 | 3/2011 | Atanasoska et al. |
| 6,973,718 B2 | 12/2005 | Sheppard, Jr. et al. | | 7,922,756 B2 | 4/2011 | Lenz et al. |
| 6,979,346 B1 | 12/2005 | Hossainy et al. | | 7,981,441 B2 | 7/2011 | Pantelidis et al. |
| 6,979,348 B2 | 12/2005 | Sundar | | 8,029,816 B2 | 10/2011 | Hossainy et al. |
| 6,984,404 B1 | 1/2006 | Talton et al. | | 2001/0001834 A1 | 5/2001 | Palmaz et al. |
| 6,991,804 B2 | 1/2006 | Helmus et al. | | 2001/0002000 A1 | 5/2001 | Kumar et al. |
| 7,001,421 B2 | 2/2006 | Cheng et al. | | 2001/0002435 A1 | 5/2001 | Berg et al. |
| 7,011,680 B2 | 3/2006 | Alt | | 2001/0013166 A1 | 8/2001 | Yan |
| 7,014,654 B2 | 3/2006 | Welsh et al. | | 2001/0014717 A1 | 8/2001 | Hossainy et al. |
| 7,018,408 B2 | 3/2006 | Bailey et al. | | 2001/0014821 A1 | 8/2001 | Juman et al. |
| 7,041,130 B2 | 5/2006 | Santini, Jr. et al. | | 2001/0027299 A1 | 10/2001 | Yang et al. |
| 7,048,939 B2 | 5/2006 | Elkins et al. | | 2001/0029660 A1 | 10/2001 | Johnson |
| 7,052,488 B2 | 5/2006 | Uhland | | 2001/0032011 A1 | 10/2001 | Stanford |
| 7,056,338 B2 | 6/2006 | Shanley et al. | | 2001/0032013 A1 | 10/2001 | Marton |
| 7,056,339 B2 | 6/2006 | Elkins et al. | | 2001/0044651 A1 | 11/2001 | Steinke et al. |
| 7,056,591 B1 | 6/2006 | Pacetti et al. | | 2002/0000175 A1 | 1/2002 | Hintermaier et al. |
| 7,060,051 B2 | 6/2006 | Palasis | | 2002/0004060 A1 | 1/2002 | Heublein et al. |
| 7,063,748 B2 | 6/2006 | Talton | | 2002/0007102 A1 | 1/2002 | Salmon et al. |
| 7,066,234 B2 | 6/2006 | Sawitowski | | 2002/0007209 A1 | 1/2002 | Schearder et al. |
| 7,077,859 B2 | 7/2006 | Sirhan et al. | | 2002/0009604 A1 | 1/2002 | Zamora et al. |
| 7,078,108 B2 | 7/2006 | Zhang et al. | | 2002/0010505 A1 | 1/2002 | Richter |
| 7,083,642 B2 | 8/2006 | Sirhan et al. | | 2002/0016623 A1 | 2/2002 | Kula et al. |
| 7,087,661 B1 | 8/2006 | Alberte et al. | | 2002/0016624 A1 | 2/2002 | Patterson et al. |
| 7,099,091 B2 | 8/2006 | Taniguchi et al. | | 2002/0028827 A1 | 3/2002 | Naicker et al. |
| 7,101,391 B2 | 9/2006 | Scheuermann et al. | | 2002/0032477 A1 | 3/2002 | Helmus et al. |
| 7,101,394 B2 | 9/2006 | Hamm et al. | | 2002/0038146 A1 | 3/2002 | Harry |
| 7,105,018 B1 | 9/2006 | Yip et al. | | 2002/0042039 A1 | 4/2002 | Kim et al. |
| 7,105,199 B2 | 9/2006 | Blinn et al. | | 2002/0051730 A1 | 5/2002 | Bodnar et al. |
| 7,144,840 B2 | 12/2006 | Yeung et al. | | 2002/0051846 A1 | 5/2002 | Kirkpatrick et al. |
| 7,160,592 B2 | 1/2007 | Rypacek et al. | | 2002/0052288 A1 | 5/2002 | Krell et al. |
| 7,163,715 B1 | 1/2007 | Kramer | | 2002/0065553 A1 | 5/2002 | Weber |
| 7,169,177 B2 | 1/2007 | Obara | | 2002/0072734 A1 | 6/2002 | Liedtke et al. |
| 7,169,178 B1 | 1/2007 | Santos et al. | | 2002/0077520 A1 | 6/2002 | Segal et al. |
| 7,195,640 B2 | 3/2007 | Falotico et al. | | 2002/0077693 A1 | 6/2002 | Barclay et al. |
| 7,195,641 B2 | 3/2007 | Palmaz et al. | | 2002/0087123 A1 | 7/2002 | Hossainy et al. |
| 7,198,675 B2 | 4/2007 | Fox et al. | | 2002/0091375 A1 | 7/2002 | Sahatjian et al. |
| 7,208,011 B2 | 4/2007 | Shanley et al. | | 2002/0095871 A1 | 7/2002 | McArdle et al. |
| 7,208,172 B2 | 4/2007 | Birdsall et al. | | 2002/0098278 A1 | 7/2002 | Bates et al. |
| 7,208,190 B2 | 4/2007 | Verlee et al. | | 2002/0099359 A1 | 7/2002 | Santini, Jr. et al. |
| 7,229,471 B2 | 6/2007 | Gale et al. | | 2002/0099438 A1 | 7/2002 | Furst |
| 7,235,096 B1 | 6/2007 | Van Tassel et al. | | 2002/0103527 A1 | 8/2002 | Kocur et al. |

| | | | | | |
|---|---|---|---|---|---|
| 2002/0103528 A1 | 8/2002 | Schaldach et al. | 2003/0167878 A1 | 9/2003 | Al-Salim et al. |
| 2002/0104599 A1 | 8/2002 | Tillotson et al. | 2003/0170605 A1 | 9/2003 | Long et al. |
| 2002/0121497 A1 | 9/2002 | Tomonto | 2003/0181975 A1 | 9/2003 | Ishii et al. |
| 2002/0123801 A1 | 9/2002 | Pacetti et al. | 2003/0185895 A1 | 10/2003 | Lanphere et al. |
| 2002/0133222 A1 | 9/2002 | Das | 2003/0185964 A1 | 10/2003 | Weber et al. |
| 2002/0133225 A1 | 9/2002 | Gordon | 2003/0190406 A1 | 10/2003 | Hossainy et al. |
| 2002/0138100 A1 | 9/2002 | Stoll et al. | 2003/0195613 A1 | 10/2003 | Curcio et al. |
| 2002/0138136 A1 | 9/2002 | Chandresekaran et al. | 2003/0203991 A1 | 10/2003 | Schottman et al. |
| 2002/0140137 A1 | 10/2002 | Sapieszko et al. | 2003/0204168 A1 | 10/2003 | Bosma et al. |
| 2002/0142579 A1 | 10/2002 | Vincent et al. | 2003/0208256 A1 | 11/2003 | DiMatteo et al. |
| 2002/0144757 A1 | 10/2002 | Craig et al. | 2003/0211135 A1 | 11/2003 | Greenhalgh et al. |
| 2002/0155212 A1 | 10/2002 | Hossainy | 2003/0216803 A1 | 11/2003 | Ledergerber |
| 2002/0165265 A1 | 11/2002 | Hunter et al. | 2003/0216806 A1 | 11/2003 | Togawa et al. |
| 2002/0165600 A1 | 11/2002 | Banas et al. | 2003/0219562 A1 | 11/2003 | Rypacek et al. |
| 2002/0165607 A1 | 11/2002 | Alt | 2003/0225450 A1 | 12/2003 | Shulze et al. |
| 2002/0167118 A1 | 11/2002 | Billiet et al. | 2003/0236323 A1 | 12/2003 | Ratner et al. |
| 2002/0168466 A1 | 11/2002 | Tapphorn et al. | 2003/0236514 A1 | 12/2003 | Schwarz |
| 2002/0169493 A1 | 11/2002 | Widenhouse et al. | 2004/0000540 A1 | 1/2004 | Soboyejo et al. |
| 2002/0178570 A1 | 12/2002 | Sogard et al. | 2004/0002755 A1 | 1/2004 | Fischell et al. |
| 2002/0182241 A1 | 12/2002 | Borenstein et al. | 2004/0006382 A1 | 1/2004 | Sohier |
| 2002/0183581 A1 | 12/2002 | Yoe et al. | 2004/0013873 A1 | 1/2004 | Wendorff et al. |
| 2002/0183682 A1 | 12/2002 | Darvish et al. | 2004/0016651 A1 | 1/2004 | Windler |
| 2002/0187260 A1 | 12/2002 | Sheppard, Jr. et al. | 2004/0018296 A1 | 1/2004 | Castro et al. |
| 2002/0193336 A1 | 12/2002 | Elkins et al. | 2004/0019376 A1 | 1/2004 | Alt |
| 2002/0193869 A1 | 12/2002 | Dang | 2004/0022824 A1 | 2/2004 | Li et al. |
| 2002/0197178 A1 | 12/2002 | Yan | 2004/0026811 A1 | 2/2004 | Murphy et al. |
| 2002/0198601 A1 | 12/2002 | Bales et al. | 2004/0028875 A1 | 2/2004 | Van Rijn et al. |
| 2003/0003160 A1 | 1/2003 | Pugh et al. | 2004/0029303 A1 | 2/2004 | Hart et al. |
| 2003/0003220 A1 | 1/2003 | Zhong et al. | 2004/0029706 A1 | 2/2004 | Barrera et al. |
| 2003/0004563 A1 | 1/2003 | Jackson et al. | 2004/0030218 A1 | 2/2004 | Kocur et al. |
| 2003/0004564 A1 | 1/2003 | Elkins et al. | 2004/0030377 A1 | 2/2004 | Dubson et al. |
| 2003/0006250 A1 | 1/2003 | Tapphorn et al. | 2004/0039438 A1 | 2/2004 | Alt |
| 2003/0009214 A1 | 1/2003 | Shanley | 2004/0039441 A1 | 2/2004 | Rowland et al. |
| 2003/0009233 A1 | 1/2003 | Blinn et al. | 2004/0044397 A1 | 3/2004 | Stinson |
| 2003/0018380 A1 | 1/2003 | Craig et al. | 2004/0047980 A1 | 3/2004 | Pacetti et al. |
| 2003/0018381 A1 | 1/2003 | Whitcher et al. | 2004/0052861 A1 | 3/2004 | Hatcher et al. |
| 2003/0021820 A1 | 1/2003 | Ahola et al. | 2004/0058858 A1 | 3/2004 | Hu |
| 2003/0023300 A1 | 1/2003 | Bailey et al. | 2004/0059290 A1 | 3/2004 | Palasis |
| 2003/0028242 A1 | 2/2003 | Vallana et al. | 2004/0059407 A1 | 3/2004 | Escamilla et al. |
| 2003/0028243 A1 | 2/2003 | Bates et al. | 2004/0059409 A1 | 3/2004 | Stenzel |
| 2003/0032892 A1 | 2/2003 | Erlach et al. | 2004/0067301 A1 | 4/2004 | Ding |
| 2003/0033007 A1 | 2/2003 | Sirhan et al. | 2004/0071861 A1 | 4/2004 | Mandrusov et al. |
| 2003/0044446 A1 | 3/2003 | Moro et al. | 2004/0073284 A1 | 4/2004 | Bates et al. |
| 2003/0047028 A1 | 3/2003 | Kunitake et al. | 2004/0073298 A1 | 4/2004 | Hossainy |
| 2003/0047505 A1 | 3/2003 | Grimes et al. | 2004/0078071 A1 | 4/2004 | Escamilla et al. |
| 2003/0050687 A1 | 3/2003 | Schwade et al. | 2004/0086674 A1 | 5/2004 | Holman |
| 2003/0059640 A1 | 3/2003 | Marton et al. | 2004/0088038 A1 | 5/2004 | Dehnad et al. |
| 2003/0060871 A1 | 3/2003 | Hill et al. | 2004/0088041 A1 | 5/2004 | Stanford |
| 2003/0060873 A1 | 3/2003 | Gertner et al. | 2004/0092653 A1 | 5/2004 | Ruberti et al. |
| 2003/0060877 A1 | 3/2003 | Falotico et al. | 2004/0093071 A1 | 5/2004 | Jang |
| 2003/0064095 A1 | 4/2003 | Martin et al. | 2004/0093076 A1 | 5/2004 | White et al. |
| 2003/0069631 A1 | 4/2003 | Stoll | 2004/0098089 A1 | 5/2004 | Weber |
| 2003/0074053 A1 | 4/2003 | Palmaz et al. | 2004/0098119 A1 | 5/2004 | Wang |
| 2003/0074075 A1 | 4/2003 | Thomas et al. | 2004/0102758 A1 | 5/2004 | Davila et al. |
| 2003/0074081 A1 | 4/2003 | Ayers | 2004/0106984 A1 | 6/2004 | Stinson |
| 2003/0077200 A1 | 4/2003 | Craig et al. | 2004/0106985 A1 | 6/2004 | Jang |
| 2003/0083614 A1 | 5/2003 | Eisert | 2004/0106987 A1 | 6/2004 | Palasis et al. |
| 2003/0083646 A1 | 5/2003 | Sirhan et al. | 2004/0106994 A1 | 6/2004 | De Maeztus Martinez et al. |
| 2003/0083731 A1 | 5/2003 | Kramer et al. | 2004/0111150 A1 | 6/2004 | Berg et al. |
| 2003/0087024 A1 | 5/2003 | Flanagan | 2004/0116999 A1 | 6/2004 | Ledergerber |
| 2003/0088307 A1 | 5/2003 | Shulze et al. | 2004/0117005 A1 | 6/2004 | Nagarada Gadde et al. |
| 2003/0088312 A1 | 5/2003 | Kopia et al. | 2004/0117008 A1 | 6/2004 | Wnendt et al. |
| 2003/0100865 A1 | 5/2003 | Santini, Jr. et al. | 2004/0122504 A1 | 6/2004 | Hogendijk |
| 2003/0104028 A1 | 6/2003 | Hossainy et al. | 2004/0126566 A1 | 7/2004 | Axen et al. |
| 2003/0105511 A1 | 6/2003 | Welsh et al. | 2004/0133270 A1 | 7/2004 | Grandt |
| 2003/0108659 A1 | 6/2003 | Bales et al. | 2004/0134886 A1 | 7/2004 | Wagner et al. |
| 2003/0114917 A1 | 6/2003 | Holloway et al. | 2004/0142014 A1 | 7/2004 | Litvack et al. |
| 2003/0114921 A1 | 6/2003 | Yoon | 2004/0143317 A1 | 7/2004 | Stinson et al. |
| 2003/0118649 A1 | 6/2003 | Gao et al. | 2004/0143321 A1 | 7/2004 | Litvack et al. |
| 2003/0125803 A1 | 7/2003 | Vallana et al. | 2004/0148010 A1 | 7/2004 | Rush |
| 2003/0130206 A1 | 7/2003 | Koziak et al. | 2004/0148015 A1 | 7/2004 | Lye et al. |
| 2003/0130718 A1 | 7/2003 | Palmas et al. | 2004/0158308 A1 | 8/2004 | Hogendijk et al. |
| 2003/0138645 A1 | 7/2003 | Gleason et al. | 2004/0167572 A1 | 8/2004 | Roth et al. |
| 2003/0139799 A1 | 7/2003 | Ley et al. | 2004/0167612 A1 | 8/2004 | Grignani et al. |
| 2003/0144728 A1 | 7/2003 | Scheuermann et al. | 2004/0171978 A1 | 9/2004 | Shalaby |
| 2003/0150380 A1 | 8/2003 | Yoe | 2004/0172124 A1 | 9/2004 | Vallana et al. |
| 2003/0153901 A1 | 8/2003 | Herweck et al. | 2004/0178523 A1 | 9/2004 | Kim et al. |
| 2003/0153971 A1 | 8/2003 | Chandresekaran | 2004/0181252 A1 | 9/2004 | Boyle et al. |
| 2003/0158598 A1 | 8/2003 | Ashton et al. | 2004/0181275 A1 | 9/2004 | Noble et al. |

| | | | | | |
|---|---|---|---|---|---|
| 2004/0181276 A1 | 9/2004 | Brown et al. | 2005/0129727 A1 | 6/2005 | Weber et al. |
| 2004/0185168 A1 | 9/2004 | Weber et al. | 2005/0131509 A1 | 6/2005 | Atanasoska et al. |
| 2004/0191293 A1 | 9/2004 | Claude | 2005/0131521 A1 | 6/2005 | Marton |
| 2004/0191404 A1 | 9/2004 | Hossainy et al. | 2005/0131522 A1 | 6/2005 | Stinson et al. |
| 2004/0202692 A1 | 10/2004 | Shanley et al. | 2005/0136090 A1 | 6/2005 | Falotico et al. |
| 2004/0202773 A1* | 10/2004 | Verlee et al. ................ 427/2.1 | 2005/0137677 A1 | 6/2005 | Rush |
| 2004/0204750 A1 | 10/2004 | Dinh | 2005/0137679 A1 | 6/2005 | Changelian et al. |
| 2004/0211362 A1 | 10/2004 | Castro et al. | 2005/0137684 A1 | 6/2005 | Changelian et al. |
| 2004/0215169 A1 | 10/2004 | Li | 2005/0149102 A1 | 7/2005 | Radisch et al. |
| 2004/0215313 A1 | 10/2004 | Cheng | 2005/0149170 A1 | 7/2005 | Tassel et al. |
| 2004/0219214 A1 | 11/2004 | Gravett et al. | 2005/0159804 A1 | 7/2005 | Lad et al. |
| 2004/0220510 A1 | 11/2004 | Koullick et al. | 2005/0159805 A1 | 7/2005 | Weber et al. |
| 2004/0220662 A1 | 11/2004 | Dang et al. | 2005/0160600 A1 | 7/2005 | Bien et al. |
| 2004/0224001 A1 | 11/2004 | Pacetti et al. | 2005/0163954 A1 | 7/2005 | Shaw |
| 2004/0225346 A1 | 11/2004 | Mazumder et al. | 2005/0165467 A1 | 7/2005 | Hunter et al. |
| 2004/0225347 A1 | 11/2004 | Lang | 2005/0165468 A1 | 7/2005 | Marton |
| 2004/0228905 A1 | 11/2004 | Greenspan et al. | 2005/0165476 A1 | 7/2005 | Furst et al. |
| 2004/0230176 A1 | 11/2004 | Shanahan et al. | 2005/0171595 A1 | 8/2005 | Feldman et al. |
| 2004/0230290 A1 | 11/2004 | Weber et al. | 2005/0180919 A1 | 8/2005 | Tedeschi |
| 2004/0230293 A1 | 11/2004 | Yip et al. | 2005/0182478 A1 | 8/2005 | Holman et al. |
| 2004/0234737 A1 | 11/2004 | Pacetti | 2005/0186250 A1 | 8/2005 | Gertner et al. |
| 2004/0234748 A1 | 11/2004 | Stenzel | 2005/0187608 A1 | 8/2005 | O'Hara |
| 2004/0236399 A1 | 11/2004 | Sundar | 2005/0192657 A1 | 9/2005 | Colen et al. |
| 2004/0236415 A1 | 11/2004 | Thomas | 2005/0192664 A1 | 9/2005 | Eisert |
| 2004/0236416 A1 | 11/2004 | Falotico | 2005/0196424 A1 | 9/2005 | Chappa |
| 2004/0237282 A1 | 12/2004 | Hines | 2005/0196518 A1 | 9/2005 | Stenzel |
| 2004/0242106 A1 | 12/2004 | Rabasco et al. | 2005/0197687 A1 | 9/2005 | Molaei et al. |
| 2004/0243217 A1 | 12/2004 | Andersen et al. | 2005/0197689 A1 | 9/2005 | Molaei |
| 2004/0243241 A1 | 12/2004 | Istephanous | 2005/0203606 A1 | 9/2005 | Vancamp |
| 2004/0247671 A1 | 12/2004 | Prescott et al. | 2005/0208098 A1 | 9/2005 | Castro et al. |
| 2004/0249444 A1 | 12/2004 | Reiss | 2005/0208100 A1 | 9/2005 | Weber et al. |
| 2004/0249449 A1 | 12/2004 | Shanley et al. | 2005/0209681 A1 | 9/2005 | Curcio et al. |
| 2004/0254635 A1 | 12/2004 | Shanley et al. | 2005/0211680 A1 | 9/2005 | Li et al. |
| 2004/0261702 A1 | 12/2004 | Grabowy et al. | 2005/0214951 A1 | 9/2005 | Nahm et al. |
| 2005/0002865 A1 | 1/2005 | Klaveness et al. | 2005/0216074 A1 | 9/2005 | Sahatjian et al. |
| 2005/0004663 A1 | 1/2005 | Llanos et al. | 2005/0216075 A1 | 9/2005 | Wang et al. |
| 2005/0010275 A1 | 1/2005 | Sahatjian et al. | 2005/0220853 A1 | 10/2005 | Dao et al. |
| 2005/0015142 A1 | 1/2005 | Austin et al. | 2005/0221072 A1 | 10/2005 | Dubrow et al. |
| 2005/0019265 A1 | 1/2005 | Hammer et al. | 2005/0228477 A1 | 10/2005 | Grainger et al. |
| 2005/0019371 A1 | 1/2005 | Anderson et al. | 2005/0228491 A1 | 10/2005 | Snyder et al. |
| 2005/0020614 A1 | 1/2005 | Prescott et al. | 2005/0232968 A1 | 10/2005 | Palmaz et al. |
| 2005/0021127 A1 | 1/2005 | Kawula | 2005/0233965 A1 | 10/2005 | Schwartz et al. |
| 2005/0021128 A1 | 1/2005 | Nakahama et al. | 2005/0244459 A1 | 11/2005 | DeWitt et al. |
| 2005/0027350 A1 | 2/2005 | Momma et al. | 2005/0251245 A1 | 11/2005 | Sieradzki et al. |
| 2005/0033411 A1 | 2/2005 | Wu et al. | 2005/0251249 A1 | 11/2005 | Sahatjian et al. |
| 2005/0033412 A1 | 2/2005 | Wu et al. | 2005/0255707 A1 | 11/2005 | Hart et al. |
| 2005/0033417 A1 | 2/2005 | Borges et al. | 2005/0261760 A1 | 11/2005 | Weber |
| 2005/0037047 A1 | 2/2005 | Song | 2005/0266039 A1 | 12/2005 | Weber |
| 2005/0038498 A1 | 2/2005 | Dubrow et al. | 2005/0266040 A1 | 12/2005 | Gerberding |
| 2005/0042288 A1 | 2/2005 | Koblish et al. | 2005/0267561 A1 | 12/2005 | Jones et al. |
| 2005/0055080 A1 | 3/2005 | Istephanous et al. | 2005/0271703 A1 | 12/2005 | Anderson et al. |
| 2005/0055085 A1 | 3/2005 | Rivron et al. | 2005/0271706 A1 | 12/2005 | Anderson et al. |
| 2005/0060020 A1 | 3/2005 | Jenson | 2005/0276837 A1 | 12/2005 | Anderson et al. |
| 2005/0060021 A1 | 3/2005 | O'Brien et al. | 2005/0278016 A1 | 12/2005 | Welsh et al. |
| 2005/0069630 A1 | 3/2005 | Fox et al. | 2005/0278021 A1 | 12/2005 | Bates et al. |
| 2005/0070989 A1 | 3/2005 | Lye et al. | 2005/0281863 A1 | 12/2005 | Anderson et al. |
| 2005/0070990 A1 | 3/2005 | Stinson | 2005/0285073 A1 | 12/2005 | Singh et al. |
| 2005/0070996 A1 | 3/2005 | Dinh et al. | 2005/0287188 A1 | 12/2005 | Anderson et al. |
| 2005/0072544 A1 | 4/2005 | Palmaz et al. | 2006/0013850 A1 | 1/2006 | Domb |
| 2005/0074479 A1 | 4/2005 | Weber et al. | 2006/0015175 A1 | 1/2006 | Palmaz et al. |
| 2005/0074545 A1 | 4/2005 | Thomas | 2006/0015361 A1 | 1/2006 | Sattler et al. |
| 2005/0077305 A1 | 4/2005 | Guevara | 2006/0020742 A1 | 1/2006 | Au et al. |
| 2005/0079199 A1 | 4/2005 | Heruth et al. | 2006/0025848 A1 | 2/2006 | Weber et al. |
| 2005/0079201 A1 | 4/2005 | Rathenow et al. | 2006/0034884 A1 | 2/2006 | Stenzel |
| 2005/0079356 A1 | 4/2005 | Rathenow et al. | 2006/0035026 A1 | 2/2006 | Atanasoska et al. |
| 2005/0087520 A1 | 4/2005 | Wang et al. | 2006/0038027 A1 | 2/2006 | O'Connor et al. |
| 2005/0092615 A1 | 5/2005 | Birdsall et al. | 2006/0051397 A1 | 3/2006 | Maier et al. |
| 2005/0096731 A1 | 5/2005 | Looi et al. | 2006/0052744 A1 | 3/2006 | Weber |
| 2005/0100577 A1 | 5/2005 | Parker et al. | 2006/0052863 A1 | 3/2006 | Harder et al. |
| 2005/0100609 A1 | 5/2005 | Claude | 2006/0052864 A1 | 3/2006 | Harder et al. |
| 2005/0102025 A1 | 5/2005 | Laroche et al. | 2006/0062820 A1 | 3/2006 | Gertner et al. |
| 2005/0106212 A1 | 5/2005 | Gertner et al. | 2006/0069427 A1 | 3/2006 | Savage et al. |
| 2005/0107869 A1 | 5/2005 | Sirhan et al. | 2006/0075044 A1 | 4/2006 | Fox et al. |
| 2005/0107870 A1 | 5/2005 | Wang et al. | 2006/0075092 A1 | 4/2006 | Kidokoro |
| 2005/0110214 A1 | 5/2005 | Shank et al. | 2006/0079863 A1 | 4/2006 | Burgmeier et al. |
| 2005/0113798 A1 | 5/2005 | Slater et al. | 2006/0085062 A1 | 4/2006 | Lee et al. |
| 2005/0113936 A1 | 5/2005 | Brustad et al. | 2006/0085065 A1 | 4/2006 | Krause et al. |
| 2005/0118229 A1 | 6/2005 | Boiarski | 2006/0088561 A1 | 4/2006 | Eini et al. |
| 2005/0119723 A1 | 6/2005 | Peacock | 2006/0088566 A1 | 4/2006 | Parsonage et al. |

| | | | | | |
|---|---|---|---|---|---|
| 2006/0088567 A1 | 4/2006 | Warner et al. | 2007/0128245 A1 | 6/2007 | Rosenberg et al. |
| 2006/0088666 A1 | 4/2006 | Kobrin et al. | 2007/0129789 A1 | 6/2007 | Cottone et al. |
| 2006/0093643 A1 | 5/2006 | Stenzel | 2007/0134288 A1 | 6/2007 | Parsonage et al. |
| 2006/0093646 A1 | 5/2006 | Cima et al. | 2007/0135908 A1 | 6/2007 | Zhao |
| 2006/0095123 A1 | 5/2006 | Flanagan | 2007/0148251 A1 | 6/2007 | Hossainy et al. |
| 2006/0100696 A1 | 5/2006 | Atanasoska et al. | 2007/0151093 A1 | 7/2007 | Curcio et al. |
| 2006/0115512 A1 | 6/2006 | Peacock et al. | 2007/0154513 A1 | 7/2007 | Atanasoska et al. |
| 2006/0121080 A1 | 6/2006 | Lye et al. | 2007/0156231 A1 | 7/2007 | Weber |
| 2006/0122694 A1 | 6/2006 | Stinson et al. | 2007/0173923 A1 | 7/2007 | Savage et al. |
| 2006/0125144 A1 | 6/2006 | Weber et al. | 2007/0181433 A1 | 8/2007 | Birdsall et al. |
| 2006/0127442 A1 | 6/2006 | Helmus | 2007/0190104 A1 | 8/2007 | Kamath et al. |
| 2006/0127443 A1 | 6/2006 | Helmus | 2007/0191923 A1 | 8/2007 | Weber et al. |
| 2006/0129215 A1 | 6/2006 | Helmus et al. | 2007/0191928 A1 | 8/2007 | Rolando et al. |
| 2006/0129225 A1 | 6/2006 | Kopia et al. | 2007/0191931 A1 | 8/2007 | Weber et al. |
| 2006/0136048 A1 | 6/2006 | Pacetti et al. | 2007/0191943 A1 | 8/2007 | Shrivastava et al. |
| 2006/0140867 A1 | 6/2006 | Helfer et al. | 2007/0198081 A1 | 8/2007 | Castro et al. |
| 2006/0141156 A1 | 6/2006 | Viel et al. | 2007/0202466 A1 | 8/2007 | Schwarz et al. |
| 2006/0142853 A1 | 6/2006 | Wang et al. | 2007/0207186 A1 | 9/2007 | Scanlon et al. |
| 2006/0149365 A1 | 7/2006 | Fifer et al. | 2007/0208412 A1 | 9/2007 | Elmaleh |
| 2006/0153729 A1 | 7/2006 | Stinson et al. | 2007/0212547 A1 | 9/2007 | Fredrickson et al. |
| 2006/0155361 A1 | 7/2006 | Schomig et al. | 2007/0213827 A1 | 9/2007 | Arramon |
| 2006/0167543 A1 | 7/2006 | Bailey et al. | 2007/0219626 A1 | 9/2007 | Rolando et al. |
| 2006/0171985 A1 | 8/2006 | Richard et al. | 2007/0219642 A1 | 9/2007 | Richter |
| 2006/0171990 A1 | 8/2006 | Asgari | 2007/0224116 A1 | 9/2007 | Chandrasekaran et al. |
| 2006/0178727 A1 | 8/2006 | Richter | 2007/0224224 A1 | 9/2007 | Cordeira Da Silva et al. |
| 2006/0184235 A1 | 8/2006 | Rivron et al. | 2007/0224235 A1 | 9/2007 | Tenney et al. |
| 2006/0193886 A1 | 8/2006 | Owens et al. | 2007/0224244 A1 | 9/2007 | Weber et al. |
| 2006/0193887 A1 | 8/2006 | Owens et al. | 2007/0244569 A1 | 10/2007 | Weber et al. |
| 2006/0193888 A1 | 8/2006 | Lye et al. | 2007/0254091 A1 | 11/2007 | Fredrickson et al. |
| 2006/0193889 A1 | 8/2006 | Spradlin et al. | 2007/0255392 A1 | 11/2007 | Johnson |
| 2006/0193890 A1 | 8/2006 | Owens et al. | 2007/0264303 A1 | 11/2007 | Atanasoska et al. |
| 2006/0199876 A1 | 9/2006 | Troczynski et al. | 2007/0269480 A1 | 11/2007 | Richard et al. |
| 2006/0200229 A1 | 9/2006 | Burgermeister et al. | 2007/0299509 A1 | 12/2007 | Ding |
| 2006/0200231 A1 | 9/2006 | O'Brien et al. | 2008/0003251 A1 | 1/2008 | Zhou |
| 2006/0210595 A1 | 9/2006 | Singhvi et al. | 2008/0004691 A1 | 1/2008 | Weber et al. |
| 2006/0212109 A1 | 9/2006 | Sirhan et al. | 2008/0008654 A1 | 1/2008 | Clarke et al. |
| 2006/0222679 A1 | 10/2006 | Shanley et al. | 2008/0038146 A1 | 2/2008 | Wachter et al. |
| 2006/0222844 A1 | 10/2006 | Stinson | 2008/0050413 A1 | 2/2008 | Horvers et al. |
| 2006/0224234 A1 | 10/2006 | Jayaraman | 2008/0050415 A1 | 2/2008 | Atanasoska et al. |
| 2006/0229711 A1 | 10/2006 | Yan et al. | 2008/0051881 A1 | 2/2008 | Feng et al. |
| 2006/0229713 A1 | 10/2006 | Shanley et al. | 2008/0057103 A1 | 3/2008 | Roorda |
| 2006/0229715 A1 | 10/2006 | Istephanous et al. | 2008/0058921 A1 | 3/2008 | Lindquist |
| 2006/0230476 A1 | 10/2006 | Atanasoska et al. | 2008/0069854 A1 | 3/2008 | Xiao et al. |
| 2006/0233941 A1 | 10/2006 | Olson | 2008/0071348 A1 | 3/2008 | Boismier et al. |
| 2006/0251701 A1 | 11/2006 | Lynn et al. | 2008/0071349 A1 | 3/2008 | Atanasoska et al. |
| 2006/0263512 A1 | 11/2006 | Glocker | 2008/0071350 A1 | 3/2008 | Stinson |
| 2006/0263515 A1 | 11/2006 | Rieck et al. | 2008/0071351 A1 | 3/2008 | Flanagan et al. |
| 2006/0264138 A1 | 11/2006 | Sowinski et al. | 2008/0071352 A1 | 3/2008 | Weber et al. |
| 2006/0271169 A1 | 11/2006 | Lye et al. | 2008/0071353 A1 | 3/2008 | Weber et al. |
| 2006/0275554 A1 | 12/2006 | Zhao et al. | 2008/0071355 A1 | 3/2008 | Weber et al. |
| 2006/0276877 A1 | 12/2006 | Owens et al. | 2008/0071358 A1 | 3/2008 | Weber et al. |
| 2006/0276878 A1 | 12/2006 | Owens et al. | 2008/0086198 A1 | 4/2008 | Owens et al. |
| 2006/0276879 A1 | 12/2006 | Lye et al. | 2008/0086199 A1 | 4/2008 | Dave et al. |
| 2006/0276884 A1 | 12/2006 | Lye et al. | 2008/0086201 A1 | 4/2008 | Weber et al. |
| 2006/0276885 A1 | 12/2006 | Lye et al. | 2008/0097577 A1 | 4/2008 | Atanasoska et al. |
| 2006/0276910 A1 | 12/2006 | Weber | 2008/0107890 A1 | 5/2008 | Bureau et al. |
| 2006/0280770 A1 | 12/2006 | Hossainy et al. | 2008/0124373 A1 | 5/2008 | Xiao et al. |
| 2006/0292388 A1 | 12/2006 | Palumbo et al. | 2008/0140186 A1 | 6/2008 | Grignani et al. |
| 2007/0003589 A1 | 1/2007 | Astafieva et al. | 2008/0145400 A1 | 6/2008 | Weber et al. |
| 2007/0003817 A1 | 1/2007 | Umeda et al. | 2008/0147177 A1 | 6/2008 | Scheuermann et al. |
| 2007/0032858 A1 | 2/2007 | Santos et al. | 2008/0152929 A1 | 6/2008 | Zhao |
| 2007/0032864 A1 | 2/2007 | Furst et al. | 2008/0160259 A1 | 7/2008 | Nielson et al. |
| 2007/0036905 A1 | 2/2007 | Kramer | 2008/0171929 A1 | 7/2008 | Katims |
| 2007/0038176 A1 | 2/2007 | Weber et al. | 2008/0188836 A1 | 8/2008 | Weber et al. |
| 2007/0038289 A1 | 2/2007 | Nishide et al. | 2008/0241218 A1 | 10/2008 | McMorrow et al. |
| 2007/0048452 A1 | 3/2007 | Feng et al. | 2008/0243231 A1 | 10/2008 | Flanagan et al. |
| 2007/0052497 A1 | 3/2007 | Tada | 2008/0243240 A1 | 10/2008 | Doty et al. |
| 2007/0055349 A1 | 3/2007 | Santos et al. | 2008/0249600 A1 | 10/2008 | Atanasoska et al. |
| 2007/0055354 A1 | 3/2007 | Santos et al. | 2008/0249615 A1 | 10/2008 | Weber |
| 2007/0059435 A1 | 3/2007 | Santos et al. | 2008/0255508 A1 | 10/2008 | Wang |
| 2007/0065418 A1 | 3/2007 | Vallana et al. | 2008/0255657 A1 | 10/2008 | Gregorich et al. |
| 2007/0071789 A1 | 3/2007 | Pantelidis et al. | 2008/0262607 A1 | 10/2008 | Fricke |
| 2007/0072978 A1 | 3/2007 | Zoromski et al. | 2008/0275543 A1 | 11/2008 | Lenz et al. |
| 2007/0073385 A1 | 3/2007 | Schaeffer et al. | 2008/0288048 A1 | 11/2008 | Rolando et al. |
| 2007/0073390 A1 | 3/2007 | Lee | 2008/0290467 A1 | 11/2008 | Shue et al. |
| 2007/0106347 A1 | 5/2007 | Lin | 2008/0294236 A1 | 11/2008 | Anand et al. |
| 2007/0110888 A1 | 5/2007 | Radhakrishnan et al. | 2008/0294246 A1 | 11/2008 | Scheuermann et al. |
| 2007/0112421 A1 | 5/2007 | O'Brien | 2008/0306584 A1 | 12/2008 | Kramer-Brown |
| 2007/0123973 A1 | 5/2007 | Roth et al. | 2009/0012603 A1 | 1/2009 | Xu et al. |

| | | | | | |
|---|---|---|---|---|---|
| 2009/0018639 A1 | 1/2009 | Kuehling | AU | 2003272710 | 4/2004 |
| 2009/0018642 A1 | 1/2009 | Benco | AU | 2003285195 | 6/2004 |
| 2009/0018644 A1 | 1/2009 | Weber et al. | AU | 2003287633 | 6/2004 |
| 2009/0018647 A1 | 1/2009 | Benco et al. | AU | 2003290675 | 6/2004 |
| 2009/0028785 A1 | 1/2009 | Clarke | AU | 2003290676 | 6/2004 |
| 2009/0030504 A1 | 1/2009 | Weber et al. | AU | 2003291470 | 6/2004 |
| 2009/0076588 A1 | 3/2009 | Weber | AU | 2003295419 | 6/2004 |
| 2009/0076595 A1 | 3/2009 | Lindquist et al. | AU | 2003295535 | 6/2004 |
| 2009/0081450 A1 | 3/2009 | Ascher et al. | AU | 2003295763 | 6/2004 |
| 2009/0112310 A1 | 4/2009 | Zhang | AU | 2004202073 | 6/2004 |
| 2009/0118809 A1 | 5/2009 | Scheuermann et al. | AU | 2003300323 | 7/2004 |
| 2009/0118812 A1 | 5/2009 | Kokate et al. | AU | 2004213021 | 9/2004 |
| 2009/0118813 A1 | 5/2009 | Scheuermann et al. | AU | 2003293557 | 1/2005 |
| 2009/0118814 A1 | 5/2009 | Schoenle et al. | AU | 780539 | 3/2005 |
| 2009/0118815 A1 | 5/2009 | Arcand et al. | BR | 8701135 | 1/1988 |
| 2009/0118818 A1 | 5/2009 | Foss et al. | BR | 0207321 | 2/2004 |
| 2009/0118820 A1 | 5/2009 | Gregorich et al. | BR | 0016957 | 6/2004 |
| 2009/0118821 A1 | 5/2009 | Scheuermann et al. | BR | 0316065 | 9/2005 |
| 2009/0118822 A1 | 5/2009 | Holman et al. | BR | 0316102 | 9/2005 |
| 2009/0118823 A1 | 5/2009 | Atanasoska et al. | CA | 1283505 | 4/1991 |
| 2009/0123517 A1 | 5/2009 | Flanagan et al. | CA | 2172187 | 10/1996 |
| 2009/0123521 A1 | 5/2009 | Weber et al. | CA | 2178541 | 12/1996 |
| 2009/0138077 A1 | 5/2009 | Weber et al. | CA | 2234787 | 10/1998 |
| 2009/0149942 A1 | 6/2009 | Edelman et al. | CA | 2235031 | 10/1998 |
| 2009/0157165 A1 | 6/2009 | Miller et al. | CA | 2238837 | 2/1999 |
| 2009/0157166 A1 | 6/2009 | Singhal et al. | CA | 2340652 | 3/2000 |
| 2009/0157172 A1 | 6/2009 | Kokate et al. | CA | 2392006 | 5/2001 |
| 2009/0177273 A1 | 7/2009 | Piveteau et al. | CA | 2337565 | 8/2001 |
| 2009/0186068 A1 | 7/2009 | Miller et al. | CA | 2409862 | 11/2001 |
| 2009/0192593 A1 | 7/2009 | Meyer et al. | CA | 2353197 | 1/2002 |
| 2009/0202610 A1 | 8/2009 | Wilson | CA | 2429356 | 8/2002 |
| 2009/0208428 A1 | 8/2009 | Hill et al. | CA | 2435306 | 8/2002 |
| 2009/0220612 A1 | 9/2009 | Perera | CA | 2436241 | 8/2002 |
| 2009/0259300 A1 | 10/2009 | Dorogy, Jr. et al. | CA | 2438695 | 8/2002 |
| 2009/0264975 A1 | 10/2009 | Flanagan et al. | CA | 2460334 | 3/2003 |
| 2009/0281613 A1 | 11/2009 | Atanasoska et al. | CA | 2425665 | 4/2003 |
| 2009/0287301 A1 | 11/2009 | Weber | CA | 2465704 | 4/2003 |
| 2009/0306765 A1 | 12/2009 | Weber | CA | 2464906 | 5/2003 |
| 2009/0317766 A1 | 12/2009 | Heidenau et al. | CA | 2468677 | 6/2003 |
| 2009/0319032 A1 | 12/2009 | Weber et al. | CA | 2469744 | 6/2003 |
| 2010/0003904 A1 | 1/2010 | Duescher | CA | 2484383 | 1/2004 |
| 2010/0008970 A1 | 1/2010 | O'Brien et al. | CA | 2497602 | 4/2004 |
| 2010/0028403 A1 | 2/2010 | Scheuermann et al. | CA | 2499976 | 4/2004 |
| 2010/0030326 A1 | 2/2010 | Radhakrishnan et al. | CA | 2503625 | 5/2004 |
| 2010/0042206 A1 | 2/2010 | Yadav et al. | CA | 2504524 | 5/2004 |
| 2010/0057197 A1 | 3/2010 | Weber et al. | CA | 2505576 | 5/2004 |
| 2010/0070013 A1 | 3/2010 | Park | CA | 2513721 | 5/2004 |
| 2010/0070022 A1 | 3/2010 | Kuehling | CA | 2505080 | 6/2004 |
| 2010/0070026 A1 | 3/2010 | Ito et al. | CA | 2506622 | 6/2004 |
| 2010/0130346 A1 | 5/2010 | Laine et al. | CA | 2455670 | 7/2004 |
| 2010/0131050 A1 | 5/2010 | Zhao | CA | 2508247 | 7/2004 |
| 2010/0233226 A1 | 9/2010 | Ferain et al. | CA | 2458172 | 8/2004 |
| 2011/0034752 A1 | 2/2011 | Kessler et al. | CA | 2467797 | 11/2004 |
| | | | CA | 2258898 | 1/2005 |
| | FOREIGN PATENT DOCUMENTS | | CA | 2308177 | 1/2005 |
| AT | 288234 | 2/2005 | CA | 2475968 | 1/2005 |
| AU | 4825696 | 10/1996 | CA | 2489668 | 6/2005 |
| AU | 5588896 | 12/1996 | CA | 2490170 | 6/2005 |
| AU | 5266698 | 6/1998 | CA | 2474367 | 1/2006 |
| AU | 6663298 | 9/1998 | CA | 2374090 | 5/2007 |
| AU | 716005 | 2/2000 | CA | 2282748 | 11/2007 |
| AU | 5686499 | 3/2000 | CA | 2336650 | 1/2008 |
| AU | 2587100 | 5/2000 | CA | 2304325 | 5/2008 |
| AU | 2153600 | 6/2000 | CN | 1430491 | 7/2003 |
| AU | 1616201 | 5/2001 | CN | 1547490 | 11/2004 |
| AU | 737252 | 8/2001 | CN | 1575154 | 2/2005 |
| AU | 2317701 | 8/2001 | CN | 1585627 | 2/2005 |
| AU | 5215401 | 9/2001 | CN | 1669537 | 9/2005 |
| AU | 5890401 | 12/2001 | DE | 3516411 | 11/1986 |
| AU | 3597401 | 6/2002 | DE | 3608158 | 9/1987 |
| AU | 2002353068 | 3/2003 | DE | 19916086 | 10/1999 |
| AU | 2002365875 | 6/2003 | DE | 19855421 | 5/2000 |
| AU | 2003220153 | 9/2003 | DE | 19916315 | 9/2000 |
| AU | 2003250913 | 1/2004 | DE | 9422438 | 4/2002 |
| AU | 770395 | 2/2004 | DE | 1096902 | 5/2002 |
| AU | 2003249017 | 2/2004 | DE | 10064596 | 6/2002 |
| AU | 2003256499 | 2/2004 | DE | 10107339 | 9/2002 |
| AU | 771367 | 3/2004 | DE | 69712063 | 10/2002 |
| AU | 2003271633 | 4/2004 | DE | 10127011 | 12/2002 |

| | | | | | |
|---|---|---|---|---|---|
| DE | 10150995 | 4/2003 | EP | 1319416 | 11/2004 |
| DE | 69807634 | 5/2003 | EP | 1476882 | 11/2004 |
| DE | 69431457 | 6/2003 | EP | 1479402 | 11/2004 |
| DE | 10200387 | 8/2003 | EP | 1482867 | 12/2004 |
| DE | 69719161 | 10/2003 | EP | 1011529 | 1/2005 |
| DE | 02704283 | 4/2004 | EP | 0875218 | 2/2005 |
| DE | 60106962 | 4/2005 | EP | 1181903 | 2/2005 |
| DE | 60018318 | 12/2005 | EP | 1504775 | 2/2005 |
| DE | 69732439 | 1/2006 | EP | 1042997 | 3/2005 |
| DE | 69828798 | 1/2006 | EP | 1754684 | 3/2005 |
| DE | 102004044738 | 3/2006 | EP | 1520594 | 4/2005 |
| DE | 69830605 | 5/2006 | EP | 1521603 | 4/2005 |
| DE | 102005010100 | 9/2006 | EP | 1028672 | 6/2005 |
| DE | 602005001867 | 5/2008 | EP | 1539041 | 6/2005 |
| DE | 69829015 | 3/2009 | EP | 1543798 | 6/2005 |
| DK | 127987 | 9/1987 | EP | 1550472 | 6/2005 |
| DK | 914092 | 8/2002 | EP | 1328213 | 7/2005 |
| EP | 0222853 | 5/1987 | EP | 1551569 | 7/2005 |
| EP | 0129147 | 1/1990 | EP | 1554992 | 7/2005 |
| EP | 0734721 | 10/1996 | EP | 1560613 | 8/2005 |
| EP | 0650604 | 9/1998 | EP | 1562519 | 8/2005 |
| EP | 0865762 | 9/1998 | EP | 1562654 | 8/2005 |
| EP | 0875217 | 11/1998 | EP | 1570808 | 9/2005 |
| EP | 0633840 | 11/1999 | EP | 1575631 | 9/2005 |
| EP | 0953320 | 11/1999 | EP | 1575638 | 9/2005 |
| EP | 0971644 | 1/2000 | EP | 1575642 | 9/2005 |
| EP | 0982041 | 3/2000 | EP | 0900059 | 10/2005 |
| EP | 1105169 | 6/2001 | EP | 1581147 | 10/2005 |
| EP | 1124594 | 8/2001 | EP | 1586286 | 10/2005 |
| EP | 1127582 | 8/2001 | EP | 1254673 | 11/2005 |
| EP | 1131127 | 9/2001 | EP | 1261297 | 11/2005 |
| EP | 1132058 | 9/2001 | EP | 0927006 | 1/2006 |
| EP | 1150738 | 11/2001 | EP | 1621603 | 2/2006 |
| EP | 1172074 | 1/2002 | EP | 1218665 | 5/2006 |
| EP | 1181943 | 2/2002 | EP | 1222941 | 5/2006 |
| EP | 0914092 | 4/2002 | EP | 1359867 | 5/2006 |
| EP | 1216665 | 6/2002 | EP | 1656961 | 5/2006 |
| EP | 0747069 | 9/2002 | EP | 1277449 | 6/2006 |
| EP | 0920342 | 9/2002 | EP | 0836839 | 7/2006 |
| EP | 1242130 | 9/2002 | EP | 1684817 | 8/2006 |
| EP | 0623354 | 10/2002 | EP | 1687042 | 8/2006 |
| EP | 0806211 | 10/2002 | EP | 0907339 | 11/2006 |
| EP | 1275352 | 1/2003 | EP | 1359865 | 11/2006 |
| EP | 0850604 | 2/2003 | EP | 1214108 | 1/2007 |
| EP | 1280512 | 2/2003 | EP | 1416885 | 1/2007 |
| EP | 1280568 | 2/2003 | EP | 1441667 | 1/2007 |
| EP | 1280569 | 2/2003 | EP | 1192957 | 2/2007 |
| EP | 1294309 | 3/2003 | EP | 1236447 | 2/2007 |
| EP | 0824900 | 4/2003 | EP | 1764116 | 3/2007 |
| EP | 1308179 | 5/2003 | EP | 1185215 | 4/2007 |
| EP | 1310242 | 5/2003 | EP | 1442757 | 4/2007 |
| EP | 1314405 | 5/2003 | EP | 1786363 | 5/2007 |
| EP | 1316323 | 6/2003 | EP | 1787602 | 5/2007 |
| EP | 1339448 | 9/2003 | EP | 1788973 | 5/2007 |
| EP | 1347791 | 10/2003 | EP | 1796754 | 6/2007 |
| EP | 1347792 | 10/2003 | EP | 1330273 | 7/2007 |
| EP | 1348402 | 10/2003 | EP | 0900060 | 8/2007 |
| EP | 1348405 | 10/2003 | EP | 1355588 | 8/2007 |
| EP | 1359864 | 11/2003 | EP | 1355589 | 8/2007 |
| EP | 1365710 | 12/2003 | EP | 1561436 | 8/2007 |
| EP | 1379290 | 1/2004 | EP | 1863408 | 12/2007 |
| EP | 0902666 | 2/2004 | EP | 1071490 | 1/2008 |
| EP | 1460972 | 2/2004 | EP | 1096902 | 1/2008 |
| EP | 0815806 | 3/2004 | EP | 0895762 | 2/2008 |
| EP | 1400219 | 3/2004 | EP | 0916317 | 2/2008 |
| EP | 0950386 | 4/2004 | EP | 1891988 | 2/2008 |
| EP | 1461165 | 4/2004 | EP | 1402849 | 4/2008 |
| EP | 1416884 | 5/2004 | EP | 1466634 | 7/2008 |
| EP | 1424957 | 6/2004 | EP | 1572032 | 7/2008 |
| EP | 1429816 | 6/2004 | EP | 1527754 | 8/2008 |
| EP | 1448116 | 8/2004 | EP | 1968662 | 9/2008 |
| EP | 1448118 | 8/2004 | EP | 1980223 | 10/2008 |
| EP | 1449545 | 8/2004 | EP | 1988943 | 11/2008 |
| EP | 1449546 | 8/2004 | EP | 1490125 | 1/2009 |
| EP | 1254674 | 9/2004 | EP | 1829626 | 2/2009 |
| EP | 1453557 | 9/2004 | EP | 1229901 | 3/2009 |
| EP | 1457214 | 9/2004 | EP | 1128785 | 4/2009 |
| EP | 0975340 | 10/2004 | EP | 2051750 | 4/2009 |
| EP | 1466634 A | 10/2004 | EP | 1427353 | 5/2009 |

| | | | | | | |
|---|---|---|---|---|---|---|
| ES | 2169012 | 7/2002 | | WO | WO02/43796 | 6/2002 |
| FR | 2867059 | 9/2005 | | WO | WO02/47581 | 6/2002 |
| GB | 2397233 | 7/2004 | | WO | WO02/058753 | 8/2002 |
| JP | 2003024449 | 1/2003 | | WO | WO02/060349 | 8/2002 |
| JP | 2003521274 | 7/2003 | | WO | WO02/060350 | 8/2002 |
| JP | 2003290361 | 10/2003 | | WO | WO02/060506 | 8/2002 |
| JP | 2003533333 | 11/2003 | | WO | WO02/064019 | 8/2002 |
| JP | 2004500925 | 1/2004 | | WO | WO02/065947 | 8/2002 |
| JP | 2004188314 | 7/2004 | | WO | WO02/069848 | 9/2002 |
| JP | 2004522559 | 7/2004 | | WO | WO02/074431 | 9/2002 |
| JP | 2004223264 | 8/2004 | | WO | 02/085253 A | 10/2002 |
| JP | 2004267750 | 9/2004 | | WO | WO02/076525 | 10/2002 |
| JP | 2004275748 | 10/2004 | | WO | WO02/078668 | 10/2002 |
| JP | 2004305753 | 11/2004 | | WO | WO02/083039 | 10/2002 |
| JP | 2005501654 | 1/2005 | | WO | WO02/085253 | 10/2002 |
| JP | 2005502426 | 1/2005 | | WO | WO02/085424 | 10/2002 |
| JP | 2005040584 | 2/2005 | | WO | WO02/085532 | 10/2002 |
| JP | 2005503184 | 2/2005 | | WO | WO02/096389 | 12/2002 |
| JP | 2005503240 | 2/2005 | | WO | WO03/009779 | 2/2003 |
| JP | 2005507285 | 3/2005 | | WO | WO03/022178 | 3/2003 |
| JP | 2005511139 | 4/2005 | | WO | WO03/024357 | 3/2003 |
| JP | 2005511242 | 4/2005 | | WO | WO03/026713 | 4/2003 |
| JP | 2005131364 | 5/2005 | | WO | WO03/035131 | 5/2003 |
| JP | 2005152526 | 6/2005 | | WO | WO03/037220 | 5/2003 |
| JP | 2005152527 | 6/2005 | | WO | WO03/037221 | 5/2003 |
| JP | 2005199054 | 7/2005 | | WO | WO03/037223 | 5/2003 |
| JP | 2005199058 | 7/2005 | | WO | WO03/037398 | 5/2003 |
| JP | 2008516726 | 5/2008 | | WO | WO03/039407 | 5/2003 |
| KR | 2002/0066996 | 8/2002 | | WO | WO03/045582 | 6/2003 |
| KR | 2004/0066409 | 7/2004 | | WO | WO03/047463 | 6/2003 |
| KR | 2005/0117361 | 12/2005 | | WO | WO03/051233 | 6/2003 |
| NZ | 331388 | 1/2000 | | WO | WO03/055414 | 7/2003 |
| SU | 393044 | 12/1973 | | WO | WO03/061755 | 7/2003 |
| WO | WO86/06617 | 11/1986 | | WO | WO03/072287 | 9/2003 |
| WO | WO93/06792 | 4/1993 | | WO | WO03/077802 | 9/2003 |
| WO | WO93/07934 | 4/1993 | | WO | WO03/083181 | 10/2003 |
| WO | WO93/16656 | 9/1993 | | WO | WO03/094774 | 11/2003 |
| WO | WO94/16646 | 8/1994 | | WO | WO2004/004602 | 1/2004 |
| WO | WO95/03083 | 2/1995 | | WO | WO2004/004603 | 1/2004 |
| WO | WO96/04952 | 2/1996 | | WO | WO2004/006491 | 1/2004 |
| WO | WO96/09086 | 3/1996 | | WO | WO2004/006807 | 1/2004 |
| WO | WO96/32907 | 10/1996 | | WO | WO2004/006976 | 1/2004 |
| WO | WO97/41916 | 11/1997 | | WO | WO2004/006983 | 1/2004 |
| WO | WO98/17331 | 4/1998 | | WO | WO2004/010900 | 2/2004 |
| WO | WO98/18408 | 5/1998 | | WO | WO2004/014554 | 2/2004 |
| WO | WO98/23228 | 6/1998 | | WO | WO2004/026177 | 4/2004 |
| WO | WO98/36784 | 8/1998 | | WO | WO2004/028347 | 4/2004 |
| WO | WO98/38946 | 9/1998 | | WO | WO2004/028587 | 4/2004 |
| WO | WO98/38947 | 9/1998 | | WO | WO2004/043292 | 5/2004 |
| WO | WO98/40033 | 9/1998 | | WO | WO2004/043298 | 5/2004 |
| WO | WO98/57680 | 12/1998 | | WO | WO2004/043300 | 5/2004 |
| WO | WO99/16386 | 4/1999 | | WO | WO2004/043509 | 5/2004 |
| WO | WO99/23977 | 5/1999 | | WO | WO2004/043511 | 5/2004 |
| WO | WO99/42631 | 8/1999 | | WO | WO2004/045464 | 6/2004 |
| WO | WO99/49928 | 10/1999 | | WO | WO2004/045668 | 6/2004 |
| WO | WO99/52471 | 10/1999 | | WO | WO2004/058100 | 7/2004 |
| WO | WO99/62432 | 12/1999 | | WO | WO2004/060428 | 7/2004 |
| WO | WO00/01322 | 1/2000 | | WO | WO2004/064911 | 8/2004 |
| WO | WO00/10622 | 3/2000 | | WO | WO2004/071548 | 8/2004 |
| WO | WO00/25841 | 5/2000 | | WO | WO2004/072104 | 8/2004 |
| WO | WO00/27303 | 5/2000 | | WO | 2005/086733 A | 9/2004 |
| WO | WO00/30710 | 6/2000 | | WO | WO2004/073768 | 9/2004 |
| WO | WO00/48660 | 8/2000 | | WO | WO2004/080579 | 9/2004 |
| WO | WO00/64506 | 11/2000 | | WO | WO2004/087251 | 10/2004 |
| WO | WO01/35928 | 5/2001 | | WO | WO2004/096176 | 11/2004 |
| WO | WO01/41827 | 6/2001 | | WO | WO2004/105639 | 12/2004 |
| WO | WO01/45862 | 6/2001 | | WO | WO2004/108021 | 12/2004 |
| WO | WO01/45763 | 7/2001 | | WO | WO2004/108186 | 12/2004 |
| WO | WO01/66036 | 9/2001 | | WO | WO2004/108346 | 12/2004 |
| WO | WO01/80920 | 11/2001 | | WO | WO2004/110302 | 12/2004 |
| WO | WO01/87263 | 11/2001 | | WO | WO2005/004754 | 1/2005 |
| WO | WO01/87342 | 11/2001 | | WO | WO2005/006325 | 1/2005 |
| WO | WO01/87374 | 11/2001 | | WO | WO2005/011529 | 2/2005 |
| WO | WO01/89417 | 11/2001 | | WO | WO2005/014892 | 2/2005 |
| WO | WO01/89420 | 11/2001 | | WO | WO2005/015596 | 2/2005 |
| WO | WO02/26162 | 4/2002 | | WO | WO2005/027794 | 3/2005 |
| WO | WO02/30487 | 4/2002 | | WO | WO2005/032456 | 4/2005 |
| WO | WO02/38827 | 5/2002 | | WO | WO2005/034806 | 4/2005 |
| WO | WO02/42521 | 5/2002 | | WO | WO2005/042049 | 5/2005 |

| | | |
|---|---|---|
| WO | WO2005/044361 | 5/2005 |
| WO | WO2005/049520 | 6/2005 |
| WO | WO2005/051450 | 6/2005 |
| WO | WO2005/053766 | 6/2005 |
| WO | WO2005/063318 | 7/2005 |
| WO | WO2005/072437 | 8/2005 |
| WO | WO2005/082277 | 9/2005 |
| WO | WO2005/082283 | 9/2005 |
| WO | WO2005/086733 | 9/2005 |
| WO | WO2005/089825 | 9/2005 |
| WO | 2005/091834 A | 10/2005 |
| WO | WO2005/091834 | 10/2005 |
| WO | WO2005/099621 | 10/2005 |
| WO | WO2005/099626 | 10/2005 |
| WO | WO2005/110285 | 11/2005 |
| WO | WO2005/115276 | 12/2005 |
| WO | WO2005/115496 | 12/2005 |
| WO | WO2005/117752 | 12/2005 |
| WO | WO2006/014969 | 2/2006 |
| WO | WO2006/015161 | 2/2006 |
| WO | WO2006/020742 | 2/2006 |
| WO | WO2006/029364 | 3/2006 |
| WO | WO2006/029708 | 3/2006 |
| WO | WO2006/036801 | 4/2006 |
| WO | WO2006/055275 | 5/2006 |
| WO | WO2006/061598 | 6/2006 |
| WO | WO2006/063157 | 6/2006 |
| WO | WO2006/063158 | 6/2006 |
| WO | WO2006/074549 | 7/2006 |
| WO | WO2006/083418 | 8/2006 |
| WO | WO2006/104644 | 10/2006 |
| WO | WO2006/104976 | 10/2006 |
| WO | WO2006/105256 | 10/2006 |
| WO | WO2006/107677 | 10/2006 |
| WO | WO2006/116752 | 11/2006 |
| WO | WO2006/124365 | 11/2006 |
| WO | WO2007/016961 | 2/2007 |
| WO | WO2007/034167 | 3/2007 |
| WO | WO2007/070666 | 6/2007 |
| WO | WO2007/095167 | 8/2007 |
| WO | WO2007/124137 | 11/2007 |
| WO | WO2007/126768 | 11/2007 |
| WO | WO2007/130786 | 11/2007 |
| WO | WO2007/133520 | 11/2007 |
| WO | WO2007/143433 | 12/2007 |
| WO | WO2007/145961 | 12/2007 |
| WO | WO2007/147246 | 12/2007 |
| WO | WO2008/002586 | 1/2008 |
| WO | WO2008/002778 | 1/2008 |
| WO | WO2008/024149 | 2/2008 |
| WO | WO2008/024477 | 2/2008 |
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/063539 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/134493 | 11/2008 |
| WO | WO2008/140482 | 11/2008 |
| WO | WO2008/147848 | 12/2008 |
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/020520 | 2/2009 |
| WO | WO2009/050168 | 4/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| WO | WO2009/135008 | 11/2009 |
| WO | WO2009/137786 | 11/2009 |
| WO | WO2010/030873 | 3/2010 |
| ZA | 9710342 | 6/1998 |

OTHER PUBLICATIONS

Békési et al., "Efficient Submicron Processing of Metals with Femtosecond UV Pulses," *Appl. Phys. A*, 76: 355-357 (2003).

Bu et al., "Synthesis of TiO2 Porous Thin Films by Polyethylene Glycol Templating and Chemistry of the Process," *Journal of the European Ceramic Society*, 25: 673-679 (2005).

Carp et al., "Photoinduced Reactivity of Titanium Dioxide," *Progress in Solid State Chemistry*, 32: 33-177 (2004).

Cernigoj et al., "Photocatalytically Active TiO2 Thin Films Produced by Surfactant-Assistant Sol-Gel Processing," *Thin Solid Films*, 495: 327-332 (2006).

Chen et al., "Behavior of Cultured Human Umbilical Vein Endothelial Cells on Titanium Oxie Films Fabricated by Plasma Immersion Ion Implantation and Deposition," *Surface & Coatings Technology*, 186: 270-276 (2004).

Kim et al., "Fabrication and Characterization of TiO2 Thin Film Prepared by a Layer-By-Layer Self-Assembly Method," *Thin Solid Films*, 499: 83-89 (2006).

Maehara et al., "Buildup of Multilayer Structures of Organic-Inorganic Hybrid Ultra Thin Films by Wet Process," *Thin Solid Films*, 438-439: 65-69 (2003).

Schetsky, L. McDonald, "Shape Memory Alloys", *Encyclopedia of Chemical Technology* (3rd ed.), John Wiley & Sons, vol. 20. pp. 726-736 (1982).

Zheng et al., "Synthesis of Mesoporous Silica Materials via Nonsurfactant Templated Sol-Gel Route Using Mixture of Organic Compounds as Template," *Journal of Sol-Gel Science and Technology*, 24: 81-88 (2002).

U.S. Appl. No. 11/694,436, filed Mar. 30, 2007, Atanasoska et al.

"Impressive Progress in Interventional Cardiology—From 1st Balloon Inflation to First Bioabsorbable Stent," Medical News Today, pp. 1-2, May 15, 2006, (http://www.medicalnewstoday.com/articles/43313.php).

"Inorganic Polymers", Polymer Science Learning Center, Department of Polymer Science, University of Southern Mississippi, 5 pages, [first accessed Aug. 17, 2011].

"JOMED Starts Clinical Studies on Tacrolimus-Eluting Coronary Stents," Jomed Press Release, 2 pages, Jan. 14, 2002.

"Nano PLD," PVD Products, Inc. Wilmington, MA, pp. 1-2, (2003).

"Paclitaxel"—from Wikipedia, (http://en.wikipedia.org/wiki/Paclitaxel), 12 pages, (downloaded Sep. 14, 2011).

"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).

Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.

Adanur et al., "Nanocomposite Fiber Based Web and Membrane Formation and Characterization," Journal of Industrial Textiles, vol. 36, No. 4, pp. 311-327, Apr. 2007.

Akhras, "Bare metal stent, lunar IrOx2 coated or drug-eluting stent for patients with Cad?", PowerPoint presentation, pp. 1-20, Oct. 2006.

Akhras, Comparison of Iridiumoxide Coated Stent with Paclitaxel-Eluting Stent and a Bare Metal Stent in Patients With Coronary Artery Disease; Abstract, 1 page, Oct. 2006.

Al-Lamee, "Programmable Elution Profile Coating for Drug-Eluting Stents," Medical Device Technology: Materials, pp. 12-15, Mar. 2005.

Amberg et al., "Silver Deposition on Temperature Sensitive Substrates by Means of an Inverted Cylindrical Magnetron," Poster, 1 page, 2003.

Anders, "Ion Plating and Beyond: Pushing the Limits of Energetic Deposition," Vacuum Technology & Coating, pp. 41-46, Dec. 2002.

Andersson et al., "Influence of Systematically Varied Nanoscale Topography on the Morphology of Epithelial Cells," IEEE Transactions on Nanobioscience, vol. 2, No. 2, pp. 49-57, Jun. 2003.

Andersson et al., "Nanoscale features influence epithelial cell morphology and cytokine production," Biomaterials, 2003. vol. 24, No. 20, pp. 3427-3436, (2003).

Annis et al., "An Elastomeric Vascular Prosthesis," Transactions—American Society for Artificial Internal Organs. vol. XXIV, pp. 209-214, (1978).

Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.

Antunes et al., "Characterization of Corrosion Products Formed on Steels in the First Months of Atmospheric Exposure", Materia, vol. 8, No. 1, pp. 27-34, (2003).

Armani et al., "Microfabrication Technology for Polycaprolactone, a Biodegradable Polymer," Journal of Micromechanics and Microengineering, vol. 10, pp. 80-84, (2000).

Arnold et al., "Activation of Integrin Function by Nanopatterned Adhesive Interface," ChemPhysChem, vol. 5, pp. 383-388, (2004).

Ashfold et al., "Pulsed laser ablation and deposition of thin films," Chem. Soc. Rev., vol. 33, pp. 23-31, (2004).

Asoh et al., "Conditions for Fabrication of Ideally Ordered Anodic Porous Alumina Using Pretextured Al," Journal of the Electrochemical Society, vol. 148, pp. B152-B156, (2001).

Atanasoska et al., "XPS Studies on Conducting Polymers: Polypyrrole Films Doped with Perchlorate and Polymeric Anions," Chemistry Materials vol. 4, pp. 988-994, (1992).

Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.

AxynTec product review, AxynTec Dunnschichttechnik GmbH (www.axyntec.de), pp. 1-8, (2002).

Azom, "Porous Coatings for Improved Implant Life—Total Hip Replacements," pp. 1-7, [downloaded Sep. 1, 2005], (http://www.azom.com/Details.asp?ArticleID=1900).

Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).

Barbucci et al, Micro and nano-structured surfaces: Journal of Materials Science: Materials in Medicine, vol. 14, No. 8, pp. 721-725, (2003).

Bates et al. "Description of research activites: Block copolymers," Organization for Minnesota Nanotechnology Institute, University of Minnesota, pp. 1-2, (2002).

Békési et al., "Efficient Submicron Processing of Metals with Femtosecond UV Pulses," Applied Physics A, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).

Biederman et al. "Plasma Polymer-Metal Composite Films," Plasma Deposition, Treatment and Etching of Polymers, pp. 269-320, (1990).

Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M H2SO4 in the 293-195 K Range," Journal of Electroanalytical Chemistry, vol. 461, pp. 40-51, (1999).

Bretagnol et al., "Functional Micropatterning Surface by Combination of Plasma Polymerization and Lift-Off Process," Plasma Process and Polymers, vol. 3, pp. 30-38, Nov. 14, 2005.

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Bruckner et al., "Metal plasma immersion ion implantation and deposition (MPIIID): chromium on magnesium," Surface and Coatings Technology vol. 103-104, pp. 227-230, (1998).

Burmeister et al., "Colloid Monolayers as Versatile Lithographic Masks," Langmuir, vol. 13, pp. 2983-2987, (1997).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Catledge et al, "Structure and Mechanical Properties of Functionally-Graded Nanostructured Metalloceramic Coatings," Mat. Res. Soc. Symp. Proc. vol. 778, ppU7.8.1-U7.8.6, (2003).

Catledge et al., "Structural and mechanical properties of nanostructured metalloceramic coatings on cobalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and sp3/sp2 contents of diamond-like carbon (DLC) synthesized by plasma immersion ion implantation-deposition," Surface and Coatings Technology, vol. 156, pp. 289-294, (2002).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.

Choi et al., "Synthesis and Characterization of Diamond-Like Carbon Protective AR Coating," Journal of the Korean Physical Society, vol. 45, p. S864, Dec. 2004.

Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).

Chu, "Recent developments and applications of plasma immersion ion implantation," Journal of Vacuum Science Technology, vol. B22, No. 1, pp. 289-296, Jan./Feb. 2004.

Chung et al., "Roles of discontinuities in bio-inspired adhesive pads," Journal of the Rolyal Society: Interface, vol. 2, pp. 55-61, Feb. 8, 2005.

Clark, "Micropatterning Cell Adhesiveness", Immobilized Biomolecules in Analysis, Oxford University Press, pp. 95-111, (1998).

Course: C-103, "An Introduction to Physical Vapor Deposition (PVD) Processes," Society of Vacuum Coaters, SVC Education Programs: course description and syllabus, pp. 1-4, Apr. 19, 2008.

Course: C-208, "Sputter Deposition in Manufacturing" Society of Vacuum Coaters, SVC Education Programs: course description and syllabus, pp. 1-5, Apr. 22, 2008.

Csete et al., "The existence of sub-micrometer micromechanical modulation generated by polarized UV laser illumination on polymer surfaces," Materials Science and Engineering C, vol. 23, pp. 939-944, (2003).

Curtis et al. "Cells react to nanoscale order and symmetry in their surroundings," IEEE Transactions on Nanobioscience, vol. 3, No. 1, pp. 61-65, Mar. 2004.

Curtis et al., "Nantotechniques and approaches in biotechnology," Trends in Biotechnology, vol. 19, No. 3, pp. 97-101, Mar. 2001.

Curtis et al., "New Depths in Cell Behaviour: Reactions of Cells to Nanotopography," Biochem, Soc, Symp, vol. 65, pp. 15-26, (1999).

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

Curtis, "Tutorial on the biology of nanotopography," IEEE Transactions on Nanobioscience, vol. 3, No. 4, pp. 293-295, Dec. 2004.

Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.

Dalby et al., "In vitro reaction of endothelial cells to polymer demixed nanotopography," Biomaterials, vol. 23, No. 14, pp. 2945-2954, (2002).

Damen et al., "Paclitaxel Esters of Malic Acid as Prodrugs with Improved Water Solubility," Bioorganic & Medicinal Chemistry, vol. 8, pp. 427-432, (2000).

D'Aquino, "Good Drug Therapy: It's Not Just the Molecule—It's the Delivery," CEP Magazine, (www.cepmagazine.org), 3 pages, Feb. 2004.

Datta et al., "Fundamental aspects and applicatio of electrochemical microfabrication," Electrochimica Acta, vol. 45, pp. 2535-2558, (2000).

De Aza et al., "Crack growth resistance of alumina, zirconia and zirconia toughened alumina ceramics for joint prostheses," Biomaterials, vol. 23, No. 3, pp. 937-945, Feb. 2002.

Debiotech, "Debiostar, An Innovative Solution for Sustained Drug Delivery," pp. 1-4, Copyright 2001, (http://www.debiotech.com/products/drugdd/stent_page_1.html).

Debiotech, "Debiostent: An Innovatice Ceramic Coating for Implantable Medical Devices," pp. 1-2, [first downloaded on Sep. 1, 2005], (http://www.debiotech.com/products/drugdd/stent_page_1.html).

Debiotech, "Debiostent: Polymer free drug eluting coating," Jun. 14, 2007, pp. 1-2, (www.debiotech.com/products/druggd/stent_page_1.html).

Debiotech, "Debiotech Obtains Exclusive Rights to an Innovative Drug Eluting Stent Technology," Press release, 1 page, Mar. 7, 2003.

Demisse, "Computational Investigation of Conducting Polythiophenes and Substituted Polythiophenes," A Thesis Submitted to the School of Graduate Studies of Addis Ababa University, Ethiopia, pp. 1-86, Jun. 2007.

Deniau et al., "Study of the polymers obtained by electroreduction of methacrylonitrile," Journal of Electroanalytical Chemistry, vol. 505, pp. 33-43, (2001).

Desai et al., "Characterization of micromachined silicon membranes for imrnunoisolation and bioseparation applications," Journal of Membrane Science, vol. 159, pp. 221-231, (1999).

Desai et al., "Use of Microfabricated 'Nanopore' Membranes as a Rate-Limiting Barrier to Diffusion of Small and Large Molecules: Possible Role in Drug Delivery" BioMEMs and Nanotechnology World, pp. 1-2, (2001).

Desai, Integrating Cells with Microsystems: Application in Tissue Engineering and Cell-Based Delivery, PowerPoint presentation, pp. 1-41, May 10, 2002.

Di Mario et al., "Drug-eluting bioabsorbable magnesium stent," Journal of Interventional Cardiology, vol. 17, Issue 6, pp. 1-5, Dec. 2004.

Di Mario, The Moonlight Study: Multicenter Objective Observational Lunar Iridium Oxide Intimal Growth Trial, PowerPoint presentation, pp. 1-10, (2002).

DTI Technology Group: Materials-Coating, "Kinetic spray coating method," www.delphi.com, 1 page, Jul. 2004.

Dumas et al., "Characterization of magnesium fluoride thin films produced by argon ion beam-assisted deposition," Thin Solid Films, vol. 382, pp. 61-68, (2001).

Duncan et al., "Polymer-drug conjugates, PDEPT and PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

EAG Technical Note, "Functional Sites on Non-polymeric Materials: Gas Plasma Treatment and Surface Analysis," Evans Analytical Group, pp. 1-2, (2003).

Eberli et al., "The Lunar Coronary Stent System," Handbook of coronary stents, 4th edition, Chapter 17, 11 pages, (Martin Dunitz Ltd 2002).

Eesley et al., "Thermal properties of kinetics spray A1-SiC metal-matrix composite," Journal of Materials Research, vol. 18, No. 4, pp. 855-860, Apr. 2003.

Erlebacher et al., "Evolution of nonoporosity in dealloying," Nature, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Finkelstein et al., "Local drug delivery via a coronary stent with programmable release pharmacokinetics," Circulation, vol. 107, pp. 777-784, Jan. 13, 2003.

Flemming et al., "Effects of synthetic micro- and nano-structured surfaces on cell behavior," Biomaterials, vol. 20, No. 6, pp. 573-588, (1999).

Fogarassy et al., "Laser-induced forward transfer: A new approach for the deposition of high Tc superconducting thin films," Journal of Materials Research, vol. 4, No. 5, pp. 1082-1086, Sep./Oct. 1989.

Fonseca et al., "Paclitaxel-loaded PLGA nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 3319-3323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for Volume Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, p. 1-4, Apr. 3, 2000.

Gadegaard et al., "Tubes with Controllable Internal Nanotopography," Advanced Materials, vol. 16, No. 20, pp. 1857-1860, Oct. 18, 2004.

Gao, "Chemical Vapor Deposition," Handbook of Nanophase and Nanostructured Materials, vol. 1: Synthesis, Chapter 5, (2003).

Glocker et al., "AC Reactive Sputtering with Inverted Cylindrical Magnetrons," Society of Vacuum Coaters, 43rd Annual Technical Conference Proceedings—Denver, pp. 81-85, Apr. 15-20, 2000.

Glocker et al., "Recent developments in inverted cylindrical magnetron sputtering," PowerPoint presentation, pp. 1-21, (2001).

Glocker et al., "Recent developments in inverted cylindrical magnetron sputtering," Surface and Coatings Technology, vol. 146-147, pp. 457-462, (2001).

Gollwitzer et al., "Titania Coating as Local "Drug" Delivery System with Antibacterial and Biocompatible Properties," 1 page, (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-2295, (1996).

Gorb et al., "Biological microtribology: anisotropy in frictional forces of orthopteran attachment pads reflects the unltrastructure of a highly deformable material," Proceeding of the Royal Society, London series B, vol. 267, pp. 1239-1244, (2000).

Green et al., "XPS Characterisation of Surface Modified Ni-Ti Shape Memory Alloy," Materials Science and Engineering, vol. A224, pp. 21-26, (1997).

Grubmuller, "What happens if the Room at the Bottom Runs Out? A Close Look at Small Water Pores," PNAS, vol. 100, No. 13, pp. 7421-7422, Jun. 24, 2003.

Guangliang et al., "The effects of current density on the phase composition and microstructure properties of micro-arc oxidation coating," Journal of Alloys and Compounds, vol. 345, pp. 169-200, (2002).

GVD Corporation, "Nanocoatings for a New Era," pp. 1-3, [first downloaded Nov. 12, 2003].

Haberland et al., "Filling of micron-sized contact holes with copper by energetic cluster impact," Journal of Vacuum Science Technology A, vol. 12, No. 5, pp. 2925-2930, Sep./Oct. 1994.

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harvard Nanopore, "Ion Beam Sculpting: Material Science—Fabricating Nanopores and Other Nanoscale Feature," pp. 1-5, [first downloaded Jul. 2, 2003], (http://www.mcb.harvard.edu.branton/projects-IonBeam/htm).

Hattori et al., "Photoreactivity of Sol—Gel TiO2 Films Formed on Soda-Lime Glass Substrates: Effect of SiO2 Underlayer Containing Fluorine," Langmuir, vol. 15, pp. 5422-5425, (1999).

Hau et al., "Surface-chemistry technology for microfluidics," Journal of Micromechanics and Microengineering, vol. 13, pp. 272-278, (2003).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Systhesis of Nanoclusters," 6 pages, [first downloaded Jan. 3, 2000], (http://www.fz-rossendorf.de/pls/rois/Cms?pOId=10960&pFunc=Print&pLang=de).

Helmus et al. "Surface Analysis of a Series of Copolymers of L-Glutamic Acid and L-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," KTH Chemical Science and Engineering, Stockholm, pp. 1-52, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Hrudey et al., "Organic Alq3 Nanostructures Fabricated with Glancing Angle Depostion," Vacuum Technology & Coating, pp. 1-6, May 2006.

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides II. Effect of hydration on the reduction behavior," Electrochimica Acta, vol. 45, pp. 3063-3068, (2000).

Hüppauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Ichinose et al., "A surface sol-gel process of TiO2 and other metal oxide films with molecular precision," Chem. Mater. vol. 9, pp. 1296-1298, (1997).

Ichinose et al., "Ultrathin composite films: An indispensable resource for nanotechnology," Riken Review, No. 37, pp. 34-37, Jul. 2001.

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "LUSTY" Study, Company Press Release: First clinical trial with Niobium stents, (www.tctmd.com/industry-news/one.html?news_id=3364), 1 page, Jun. 25, 2002.

Inoue et al., "Corrosion rate of magnesium and its alloys in buffered chloride solutions," Corrosion Science, vol. 44, pp. 603-610, (2002).

Inovati, "Award Winning—Environmentally-Safe, High-Quality, Metal Spray Process," Press Release, pp. 1-6, (2002), (http://www.inovati.com/papers/KM-PressRelease.doc).

Inovati, "Inovati to Develop Green Metal Coating Technology" Press Release, 1 page, [first downloaded Sep. 1, 2005], (http://www.inovati.com/papers/bmdopr.html).

Inovati, "Low temperature, high-speed sprays make novel coatings," 1 pages, [first downloaded on Mar. 18, 2003], (http://www.inovati.com/papers/ampmar01.html).

Introduction to the Metal Printing Process: Future manufacturing equipment of advanced materials and complex geometrical shapes, (www.mpp.no/intro/intro.htm), pp. 1-2, downloaded Mar. 18, 2002.

Irhayem et al., "Glucose Detection Based on Electrochemically Formed Ir Oxide Films," Journal of Electroanalytical Chemisty, vol. 538-539, pp. 153-164, (2002).

Irvine et al., Nanoscale clustering of RGD peptides at surfaces using Comb polymers. 1. Synthesis and characterization of Comb thin films, Biomacromolecules, vol. 2, No. 1, pp. 85-94, Spring 2001.

Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and P by hydrothermal treatment," Journal of Biomedical Materials Research, vol. 29, pp. 1071-1079, (1995).

Ishizawa et al., "Histomorphometric evaluation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, 1 page, Jul. 2009.

Iurhayem et al. "Glucose detection based on electrochemically formed Ir oxide films," Journal of Electroanalytical Chemistry, vol. 539-539, pp. 153-164, (2002).

JMAR LLC, "Collimated Plasma Lithography (CPL)," 1 page, [first downloaded Jul. 2, 2003], (http://www.jmar.com/co451.html).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kaplan, "Cold Gass Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Katz, "Developments in Medical Polymers for Biomaterials Applications," Medical Device Link, pp. 1-9, Jan. 2001, (http://www.devicelink.com/mddi/archive/01/01/003.html).

Kesler et al., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes—A Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Hollow Silica Spheres of Controlled Size and Porosity by Sol-Gel Processing," Journal of Americal Ceramic Society, vol. 74, Nol. 8, pp. 1987-1992, (1991).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kleinertz et al., "LUSTY Studie: Lunar STF Study," PowerPoint presentation, pp. 1-24, Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kokubo et al., "Novel bioactive materials with different mechanical properties," Biomaterials, vol. 24, pp. 2161-2175, (2003).

Kondyurin et al., "Plasma Immersion ion implantation of polyethylene," Vacuum, vol. 64, pp. 105-111, (2002).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy for Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Sep. 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kötz et al., "XPS Studies of Oxygen Evolution on Ruand RuO2 Anodes," Journal of Electrochemical Society: Electrochemical Science and Technology, pp. 825-829, Apr. 1983.

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Polyanhydrides: an overview," Advanced Drug Delivery Reviews, vol. 54, pp. 889-910, (2002).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Larner et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/LIFT.htm), pp. 1-2, downloaded Dec. 7, 2006.

Lau et al., "Hot-wire chemical vapor deposition (HWCVD) of fluorocarbon and organosilicon thin films," Thin Solid Films, vol. 395, pp. 288-291, (2001).

LaVan et al., Small-scale systems for in vivo drug delivery, Nature Biotechnology, vol. 21, No. 10, pp. 1184-1191, Oct. 2003.

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal of Applied Physics, vol. 95, No. 5, Mar. 1, 2004.

Lei et al., "Fabrication of Highly Ordered Nanoparticle Arrays Using Thin Porous Alumina Masks," Advanced Materials for Micro- and Nano-Systems (AMMNS), pp. 1-6, Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov./Dec. 1998.

Li et al., "Bioactive Hydroxyapatite Composite Coating Prepared by SOL-GEL Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "On the growth of highly ordered pores in anodized aluminum oxide," Chem. Mater., vol. 10, pp. 2470-2480, (1999).

Li et al., "Polycrystalline nanopore arrays with haxagonal ordering on aluminum," Journal of Vacuum Science Technology: A, vol. 17, pp. 1428-1431, (1999).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, pp. 1-7, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale RGD clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of SPIE, vol. 3937, pp. 44-50, (2000).

Mantis Deposition Ltd., "Nanocluster Deposition," Thame, Oxfordshire, United Kingdom, pp. 1-2, [downloaded on Feb. 2, 2007], (http://www.mantisdeposition.com/nanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. pp. 1-3, (2003).

Masuda et al., "Highly ordered nanochannel-array architecture in anodic alumina," Applied Physics Letters, vol. 71, pp. 2770-2772, (1997).

Matijević, "Colloid Chemical Aspects of Corrosion of Metals", Pure & Applied Chemisty, vol. 52, pp. 1179-1193, (1980).

Mattox, "Introduction: Physical Vapor Deposition (PVD) Processes," Vacuum Technology & Coating, pp. 60-63, Jul. 2002.

Mattox, "The History of Vacuum Coating Technology: Part V," Vacuum Technology & Coating, pp. 32-37, Oct. 2002.

Mattox, "The History of Vacuum Coating Technology: Part VI," Vacuum Technology & Coating, pp. 52-59, Oct. 2002.

Mauritz Group Homepage, "Sol-Gel Chemistry and Technology," (http://www.psrc.usin.edu/mauritz/solgel.html), pp. 1-10, (downloaded [2006]).

Meijer et al., "Laser Machining by short and ultrashort pulses, state of the art and new opportunities in the age of the photons," Annals of CIRP 2002: Manufacturing Technology, vol. 51, No. 2, pp. 531-550, (2002).

Meletis et al., "Electrolytic plasma processing for cleaning and metal-coating of steel surfaces," Surface and Coatings Technology, vol. 150, pp. 246-256, (2002).

Merriam-Webster's Dictionary Website: For definition of Strut, 1 page,[first cited Jul. 21, 2010], (http://www.merriam-webster.com/dictionary/strut).

MicroFab Technologies Inc. "MicroFab: Biomedical Applications—Stents," pp. 1-4, [first downloaded Mar. 23, 2007], (http://www.microfab.com/technology/biomedical/Stents.html).

Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).

MIV Therapeutics, "Hydroxyapatite Coating," pp. 1-4, [first downloaded Jun. 25, 2003], (http://www.mivtherapeutics.com/technology/hap/).

Mu et al., "A novel controlled release formulation for the anticancer drug paclitaxel (Taxol): PLGA nanoparticles containing vitamin E TPGS," Journal of Controlled Release, vol. 86, pp. 33-48, (2003).

Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).

Muller et al., "Solid lipid nanoparticles (SLN) for controlled drug delivery: a review of the state of the art," European Journal of Pharmaceutics and Biopharmaceutics, vol. 50, pp. 161-177, (2000).

Munchow et al., "Poly[(oligoethylene glycol) Dihydroxytitanate] as Organic-Inorganic Polymer-Electrolytes," Electrochimica Acta, vol. 45, pp. 1211-1221, (2000).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, pp. 1-9, Jun. 30, 2004.

Nanu, "Nanostructured TiO2-CuInS2 based solar cells," Symposium D, Thin Film and Nano-Structured Materials for Photovoltaics, E-MRS Spring Meeting 2003, pp. 1-2, Jun. 10-13, 2003.

NASA Glenn Research Center, "Fast Three-Dimensional Method of Modeling Atomic Oxygen Undercutting of Protected Polymers," pp. 1-6, [first downloaded on Jul. 3, 2003], (http://www.grc.nasa.gov/WWW/epbranch/suurtxt/surfaceabs.htm).

Newman et al., "Alloy Corrosion," MRS Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials—Drugs, Drug Delivery Systems, Quantum Dots and Disease Treatment," Azom.com, pp. 1-5, [first downloaded Mar. 22, 2004], (http://www.azom.com/details.asp?ArticleID=1853).

Nie et al., "Deposition of layered bioceramic hydroxyapatite/TiO2 coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

O'Brien et al., "Passivation of Nitinol Wire for Vascular Implants-A Demonstration of the Benefits," Biomaterials, vol. 23, pp. 1739-1748, (2002).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems—Nanodep60," 1 page, [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Park et al., "Multilayer Transfer Printing for Polyelectrolyte Multilayer Patterning: Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," The 22nd Annual Meeting of the Adhesion Society, pp. 1-5, Feb. 21-24, 1999.

Park et al., "Microstructural change and precipitation hardeningin melt-spun Mg-X-Ca alloys," Science and Technology of Advanced Materials, vol. 2, pp. 73-78, (2001).

Pelletier et al., "Plasma-based ion implantation and deposition: A review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pitt et al., "Attachment of hyaluronan to metallic surfaces," Journal of Biomedical Materials Research, vol. 68A, pp. 95-106, (2004).

Polygenetics, "Advanced Drug Delivery," [first downloaded on May 4, 2007], 5 pages, (http://www.polygenetics.com/drug_delivery.htm).

Ponte et al., "Porosity determination of nickel coatings on copper by anodic voltammetry," Journal of Applied Electrochemistry, vol. 32, pp. 641-646, (2002).

Prior Clinicals, Boston Scientific memo, pp. 1-2, (more than a year prior to May 23, 2007).

Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).

Pulsed Laser Deposition, (http://www.physandtech.net), pp. 1-7, Apr. 28, 2001.

PVD Materials—Materials Available for Physical Vapour Deposition (PVD) from Williams Advanced Materials. (www.azom.com), pp. 1-8, [first downloaded Apr. 28, 2006].

Qasem et al., "Kinetics of Paclitaxel 2'-N-Methylpyridinium Mesylate Decomposition," AAPS PharmSciTech, vol. 4, No. 2, Article 21, pp. 1-8, (2003).

Qiang et al., "Hard coatings (TiN, Ti$\chi$All-$\chi$N) deposited at room temperature by energetic cluster impact," Surface and Coatings Technology, 100-101, pp. 27-32, (1998).

Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.

Radin et al., "Silica sol-gel for the controlled release of antibiotics. I. Synthesis, characterization, and in vitro release," Journal of Biomedical Materials Research, vol. 27, No. 2, pp. 313-320, Nov. 2001.

Radin, et al., "In vitro bioactivity and degradation behavior of silica xerogels intended as controlled release materials," Biomaterials. vol. 23, No. 15, pp. 3113-3122, Aug. 2002.

Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).

Rees et al., "Glycoproteins in the Recognition of Substratum by Cultured Fibroblasts," Symposia of the Society for Experimental Biology: Cell-Cell Recognition, No. 32, pp. 241-260 (1978).

Rice, "Limitations of pore-stress concentrations on the mechanical properties of porous materials," Journal of Material Science, vol. 32, pp. 4731-4736, (1997).

Ristoscu, "Thin Films and Nanostructured Materials." pp. 1-2, [first downloaded Jul. 3, 2003], (http://www..fisica.unile.it/radiazioni/ThinY02Ofilms%20and%20nanostmctured%20materials.htm).

Robbie et al., "Advanced techniques for glancing angle deposition," Journal of Vacuum Science and Technology B, vol. 16, No. 3, pp. 1115-1122, (May/Jun. 1998).

Robbie et al., "Sculptured thin films and glancing angle deposition: Growth mechanics and applications," Journal of Vacuum Science Technology: A., vol. 15, pp. 1460-1465, (1997).

Roder et al., "Tuning the microstructure of pulsed laser deposited polymer-metal nanocomposites," Applied Physics A. vol. 85, pp. 15-20 (2006).

Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.

Rossi et al., "Pulsed Power Modulators for Surface Treatment by Plasma Immersion Ion Impantation," Brazilian Journal of Physics, vol. 34, No. 4B, pp. 1565-1571, Dec. 2004.

Routkevitch, "Nano- and Microfabrication with Anodic Alumina: A Route to Nanodevices," Foresight Institute 9th Conference on Molecular Nanotechnology, pp. 1-20, Nov. 8-11, 2001, Santa Clara, CA.

Santos et al., "Si-Ca-P xerogels and bone morphogenetic protein act synergistically on rat stromal marrow cell differentiation in vitro," Journal of Biomedical Materials Research, vol. 41, No. 1, pp. 87-94, Jul. 1998.

Santos et al., "Sol-Gel Derived Carrier for the Controlled Release of Proteins," Biomaterials, vol. 20, pp. 1695-1700, (1999).

Sawitowski, "Nanoporous alumina for implant coating—A novel approach towards local therapy," NanoMed 3rd Workshop, Medical Applications of Nanotechnology, Berlin, 1 page, Feb. 17-18, 2003.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces—A Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).
Schlottig et al., "Characterization of nanoscale metal structures obtained by template synthesis," Fresenius' Journal of Analytical Chemistry, vol. 361, pp. 684-686, (1998).
Schneider, "Laser Cladding with Powder: Effect of some machining parameters on clad properties," Doctoral Thesis—University of Twente, The Netherlands, pp. 1-176, ISBN 9036510988, Mar. 1998.
Selective laser sintering, from Wikipedia, (http://en.wikipedia.org/wiki/Selective_laser_sintering), pp. 1-2, downloaded on Sep. 28, 2007.
Serra et al., "Preparation of functional DNA microarrays through laser-induced forward transfer," Applied Physics Letters, vol. 85, No. 9, pp. 1639-1641, Aug. 30, 2004.
Serruys et al., "The Effect of Variable Dose and Release Kinetics on Neointimal Hyperplasia Using a Novel Paclitaxe—Eluting Stent Platform," Journal of the American College of Cardiology, vol. 46, No. 2, pp. 253-260, Jul. 19, 2005.
Sgura et al., The Lunar Stent: characteristics and clinical results, Herz, vol. 27, pp. 1-14, (2002).
Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).
Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.
Shang et al., "Structure and photocatalytic characters of TiO2 film photocatalyst coated on stainless steel webnet," Journal of Molecular Catalysis A: Chemical, vol. 202, pp. 187-1995, (2003).
Shao et al., "Fiber mats of poly(vinyl alcohol)/silica composite via Electrospinning," Materials Letters, vol. 57, pp. 1579-1584, (2003).
Shchukin et al., "Micron-scale hollow polyelectrolyte capsules with naosized magnetic Fe3O4 inside," Materials Letters, vol. 57, pp. 1743-1747, (2003).
Shevchenko et al., "Porous Surface of NiTi Alloy Produced by Plasma Ion Implantation," Institute of Ion Beam Physics and Materials Research, 1 page, May 2005.
Shevchenko, "Formation of nonoporous structures on stainless steel surface," Report, pp. 1-6, Apr. 2007.
Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).
Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology—Heart and Cardiovascular Research (Deutche Gesellschaft fur Kardiologie—Herz und Kreislaufforschung), 1 page, Oct. 30, 2005.
Silber et al., "A new stainless-steel-free stent with a potential of artifact free magnetic resonance compatibility: first clinical experience," Abstract and Poster, pp. 1-3, May 2006.
Silber, " LUSTY-FIM Study: Lunar Starflex First In Man Study, " PowerPoint presentation at the Paris Course on Revascularization, pp. 1-11, May 2003.
Silber, "Ein edelstahfreier stent aus niobium mit iridiumoxyd (IrOx)-beschichtung: Erste Ergebnisse der LUSTY-studie" (Stainless steel-free Stent out of niobium with iridiumoxyd (IrOx)-coating: Initial results of the LUSTY-study), PowerPoint presentation, pp. 1-16, Oct. 15, 2004.
Silber, "LUSTY-FIM Study: Lunar Starflex First In Man Study," PowerPoint presentation, pp. 1-16, 2003.
Silber, "Niobium/iridiumoxide Stents: LUSTY randomized trial, LUNAR ROX registry," PowerPoint presentation, pp. 1-33, 2003.
Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).

Simon et al., "Influence of topography on endothelialization of stents: Clues for new designs," Journal of Long-Term Effects of Medical Implants, Voo. 10, No. 1-2, pp. 143-151, (2000).
Sniadecki et al., "Nanotechnology for Cell-Substrate Interactions," Annals of Biomedical Engineering, vol. 34, No. 1, pp. 59-74, Jan. 1, 2006.
Sofield et al., "Ion beam modification of polymers," Nuclear Instruments and Methods in Physics Research, vol. B67, pp. 432-437, (1992).
Soler-Illia et al., "Block Copolymer-Templated Mesoporous Oxides," Current Opinion in Colloid and Interface Science, vol. 8, pp. 109-126, (2003).
Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).
Sprague et al., "Endothelial cell migration onto metal stent surfaces under static and flow conditions," Journal of Long-Term Effects of Medical Implants, vol. 10, No. 1-2, pp. 97-110, (2000).
Startschuss fur "lusty" -studie, (Launch of "lusty" -study), Cardio News, 1 page, Oct. 2002.
Stucky "High Surface Area Materials," pp. 1-5, Published: Jan. 1998, WTEC Hyper-Librarian, (http://www.wtec.org/loyola/nano/US.Review/07_03.htm).
Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.
Sundararajan et al., "Mechanisms underlying the formation of thick alumina coatings through the MAO coating technology," Surface and Coatings Technolgy, vol. 167, pp. 269-277, (2003).
Szycher et al., "Drug-Eluting Stents to Prevent Coronary Restenosis," CardioTech International, pp. 1-10, (2002).
Tabata et al., "Generalized Semiempirical Equations for the Extrapolated Range of Electronics," Nuclear Instruments and Methods, vol. 103, pp. 85-91, Mar. 28, 1972.
Takitani et al., "Desorption of Helium from Austenitic Stainless Steel Heavily Bombarded by Low Energy He Ions," Journal of Nuclear Materials, vol. 329-333, pp. 761-765, (2004).
Tamura et al., "Surface Hydroxyl Site Densities on Metal Oxides as a Measrure for the Ion-Exchange Capacity," Journal of Colloid and Interface Science, vol. 209, pp. 225-231, (1999).
Tan et al., "Corrosion and wear-corrosion behavior of NiTi modified by plasma source ion implantation," Biomaterials, vol. 24, pp. 3931-3939, (2003).
Tang et al., "Electrochemical Study of a Polarized Electrochemical Vapor Deposition Process," Journal of the Electrochemical Society, vol. 147, No. 9, pp. 3338-3344, (2000).
Tang et al., "Fabrication of Macroporous Alumina with Tailored Porosity," Jornal of American Ceramic Society, vol. 86, No. 12, pp. 2050-2054, (2003).
Tapphorn et al., "The Solid-State Spray Forming of Low-Oxide Titanium Components," Journal of Metals, vol. 50, No. 9, pp. 45-46,76, (1998).
Tassin et al., "Improvement of the Wear Resistance of 316 L Stainless Steel by Laser Surface Alloying," Surface and Coatings Technology, vol. 80, No. 9, pp. 207-210, (1996).
Terlingen, "Functionalization of Polymer Surfaces," Europlasma Technical Paper, pp. 1-29, May 8, 2004.
Terumo Europe, "Terumo Europe N.V. Enrols First Patient in Clinical Trial of the Nobori Drug-Eluting Coronary Stent," Press Release, 1 page, May 26, 2005, (http://www.terumo-europe.com/_press_release/may_26_2005.html.).
Thierry et al., "Bioactive Coatings of Endovascular Stents Based on Polyelectrolyte Multilayers," Biomacromolecules, vol. 4, pp. 1564-1571, (2003).
Tonosaki et al., "Nano-indentation testing for plasma-based ion-implanted surface of plastics," Surface and Coatings Technology, vol. 136, pp. 249-251, (2001).
Toth et al., "Ar+ laser-induced forward transfer (LIFT): a novel method for micrometer-size surface patterning," Applied Surface Science, vol. 69, pp. 317-320, (1993).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, pp. 1-2, (1997), (http://mrsec.wisc.edu/Past_projects/seedproi4/Seedproi4.html).

Uyama et al., "Surface Modifications of Polymers by Grafting," Advances in Polymer Science, vol. 139, pp. 1-39, (1998).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," pp. 1-9, [first downloaded on Nov. 12, 2003], (http://www.delftoutlook.tudelft.nl/info/index21fd.html?hoofdstuk=Article&ArtID=2243).

van der Eijk et al., " Metal Printing Process Development of a New Rapid Manufacturing Process for Metal Parts," Proceedings of the World PM2004 Conference held in Vienna, pp. 1-5, Oct. 1721, 2004.

Van Steenkiste et al., "Kinetic spray coatings," Surface & Coatings Technology, vol. 111, pp. 62-71, (1999).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of the American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "TiO2 Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vuković et al., "Anodic stability and electrochromism of electrodeposited ruthenium-iridium coatings on titanium," Journal of Electroanalytical Chemisty, vol. 330, pp. 663-673 (1992).

Wang et al., "Deposition of in-plane textured MgO on amorphous Si3N4 substrates by ion-beam-assisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres—A Novel Route to Tune Pore Morphology," Chem. Mater., vol. 13, pp. 364-371, (2001).

Webster et al." Enhanced functions of osteoblasts on nanophase ceramics," Biomaterials, vol. 21, No. 17, pp. 1803-1810, Sep. 2000.

Webster et al., "Specific proteins mediate enhanced osteoblast adhesion on nanophase ceramics," Journal of Biomedical Materials Research, vol. 5, No. 51, pp. 475-483, Sep. 2000.

Wells, "Patterned Plasma Immersion Exposure of Insulating Materials for the Purpose of Modifying Optical Properties," thesis submitted to the college of William and Mary, Williamsburg, Vriginia, pp. 1-59, Apr. 2000.

Wesolowski et al., "Surface Charge and Ion Adsorption on Metal Oxides to 290°C," Division of Chemical Sciences, Geosciences, and Biosciences, Office of Basic Energy Sciences, U.S. Department of Energy, pp. 1-6, (2001).

Whelan, "Targeted Taxane Therapy for Cancer," Drug Discovery Today, vol. 7, No. 2, pp. 90-92, Jan. 2002.

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wong et al., "Polymer segmental alignment in polarized pulsed laser-induced periodic surface structures," Applied Physics A, vol. 65, pp. 519-523, (1997).

Wood, "Next-generation drug-eluting stents tackle shortcomings of Cypher, Taxus," Heart Wire, pp. 1-6, Feb. 7, 2006, (http://www.theheart.org/article/641591.do.).

World Reference definition, "Interconnected," WorldReference.com, 1 page, [downloaded Jan. 21, 2010].

Wu et al., "Corrosion resistance of BaTiO3 films prepared by plasma electrolytic oxidation," Surface and Coatings Technology, vol. 166, pp. 31-36, (2002).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New MOCVD precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, pp. 1-27, (2003).

Yang et al., "Laser spray cladding of porous NiTi coatings on NiTi substrates," The Hong Kong Polytechnic University, 1 page, Dec. 28, 2006.

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Significance of synthetic nanostructures in dictating cellular response," Nanomedicine: Nanotechnology, Biology and Medicine, vol. 1, No. 1, pp. 10-21, Mar. 1, 2005.

Young et al., "Polarized electrochemical vapor deposition for cermet anodes in solid oxide fuel cells," Solid State Ionics, vol. 135, pp. 457-462, (2000).

Yu et al., "Enhanced photocatalytic activity of mesoporous and ordinary TiO2 thin films by sulfuric acid treatment," Applied Catalysis B: Environmental, vol. 36, pp. 31-43, (2002).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink-jet printer," Ceramics International, vol. 29, pp. 887-892, (2003).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

US 6,533,715, 03/2003, Hossainy et al. (withdrawn)

* cited by examiner

MEDICAL DEVICES WITH DRUG-ELUTING COATING

CROSS-REFERENCE TO RELATED APPLICATIONS

This application claims priority under 35 USC §119(e) to U.S. Patent Application Ser. No. 60/844,471, filed on Sep. 14, 2006, the entire contents of which are hereby incorporated by reference.

TECHNICAL FIELD

This invention relates to medical devices, such as endoprostheses (e.g., stents).

BACKGROUND

The body defines various passageways such as arteries, other blood vessels, and other body lumens. These passageways sometimes become occluded or weakened. For example, the passageways can be occluded by a tumor, restricted by a plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, or allowed to expand, so that it can contact the walls of the lumen.

Endoprostheses can be coated with biocompatible materials and/or biologically active substances, including active pharmaceutical agents.

SUMMARY

This invention is based, in part, on the discovery that applying biologically active substances (e.g., drugs) to a depression defined in a surface of a medical device (e.g., a stent) protects the substances during delivery of the device into the body. During delivery, e.g., via a catheter, biologically active substances located within such depressions remain generally undisturbed and in place, while substances located on a generally flat surface of currently-available medical devices are exposed and thus subject to shear forces that can strip the substances off the surface. The depression or depressions can be coated with a component that promotes initial adherence and subsequent elution of the biologically active substance.

In one aspect, the disclosure features a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure, and wherein one or more wall surfaces of the tubular structure bears a coating whose selected regions define at least one depression.

Embodiments may include one or more of the following features.

The surface bearing the coating defining at least one depression can be the abluminal wall surface, the luminal wall surface, the side wall surface or a combination thereof.

The coating can include at least one biologically active substance, a polymer, e.g., a biodegradable polymer, a tie layer, e.g., a biodegradable tie layer, or a combination thereof. For example, the coating can include a layer of a first biologically active substance, and a layer of a polymer and a second biologically active substance (the first and second substances can be the same or different). The polymer can be biodegradable, exposing the first substance upon erosion. The polymer, e.g., a porous polymer, can allow the first substance to diffuse through and out of the polymer. The coating can also include a ceramic layer, e.g., silica. The ceramic layer can contain, e.g., titanium (+y) oxide (−x), e.g., titanium dioxide. The coating can include titanium (+y) oxide (−x), e.g., titanium dioxide. The coating can include regions of hydrophilic and/or hydrophobic titanium (+y) oxide (−x). For example, regions of the coating that define the depression can bear a coating of hydrophobic titanium (+y) oxide (−x), e.g., hydrophobic titanium dioxide, while regions of the coating that do not define the depression can bear a coating of hydrophilic titanium (+y) oxide (−x), e.g., hydrophilic titanium dioxide, e.g., superhydrophilic titanium dioxide. In another embodiment, regions of the coating that define the depression can bear a coating of hydrophilic titanium (+y) oxide (−x), e.g., hydrophilic titanium dioxide, e.g., superhydrophilic titanium dioxide, while regions of the coating that do not define the depression can bear a coating of hydrophobic titanium (+y) oxide (−x), e.g., hydrophobic titanium dioxide. The coating can also include titanium (+y) oxide (−x) generally in one state, either hydrophilic or hydrophobic. The coating can be as thick as the depression that the coating defines is deep. The coating can be thinner than the depth of the depression that the coating defines.

The depression can be configured to extend generally along the axis of the band or connector in which the depression is defined, e.g., to extend generally in a parallel orientation to the axis of the band or connector in which the depression is defined. The depression can be configured to extend generally in traverse orientation to the axis of the band or connector in which the depression is defined, e.g., generally in a perpendicular orientation to the axis of the band or connector in which the depression is defined. The coating can define multiple depressions. The width of the depression can constitute up to about 80% of the width of the band or the connector in which the depression is defined. The depth of the depression can constitute on average up to about 50% of the thickness of the band or the connector in which the depression is defined, but locally additional depressions can constitute up to about 90% of the thickness of the band or connector.

In another aspect, the disclosure features a method of producing a medical device that includes: (a) generating a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure, and wherein one or more wall surfaces define at least one depression; and (b) applying a coating upon one or more surfaces of the medical device.

Embodiments may include one or more of the following features.

The surface that defines at least one depression can be the abluminal wall surface, the luminal wall surface, the side wall surface or a combination thereof.

The depression can be generated by laser, e.g., by a laser ablation process and/or laser-assisted chemical etching. The depression can be generated by chemical etching. The depression can be machined or formed into the raw material of the medical device, e.g., a tube, before the interconnected bands and connectors are formed. The depression can be configured to extend generally along the axis of the band or connector in which the depression is defined, e.g., to extend generally in a parallel orientation to the axis of the band or connector in which the depression is defined. The depression can be configured to extend generally in traverse orientation to the axis of the band or connector in which the depression is defined, e.g., generally in a perpendicular orientation to the axis of the band or connector in which the depression is defined. The surface can define multiple depressions. The width of the depression can constitute up to about 80% of the width of the band or the connector in which the depression is defined. The depth of the depression can constitute on average up to about 50% of the thickness of the band or the connector in which the depression is defined, but locally additional depressions can constitute up to 90% of the thickness of the band or connector.

The coating of step (b) can be applied to the depression of the abluminal surface, the luminal surface, the side surface or a combination thereof. The coating of step (b) can be applied in multiple layers.

Applying of the coating of step (b) can be carried out by dipcoating, roll coating, MicroPen® application, electrospraying, gas-assisted spraying, electrospinning or a combination thereof. Applying the coating of step (b) can be carried out by rolling the medical device over the surface of a polymer tube comprising a biologically active substance to direct the polymer and the biologically active substance into the depressions of the medical device. Applying the coating of step (b) can be carried out by forcing a mixture of a biologically active substance and a polymer through a heated nozzle into the depression.

Step (b) can further include activating the surface of the depression by, e.g., plasma treatment, ultraviolet light activation, electrical charging of desired regions of the device and texturizing.

The coating applied in step (b) can include at least one biologically active substance, a polymer, e.g., a biodegradable polymer, a tie layer, e.g., a biodegradable tie layer, or a combination thereof. For example, a first layer of coating comprising a first biologically active substance can be applied, followed by application of a second layer of coating comprising a polymer and a second biologically active substance (the first and second substances can be the same or different). The polymer can be biodegradable, exposing the first substance upon erosion. The polymer, e.g., a porous polymer, can allow the first substance to diffuse through and out of the polymer. The coating applied in step (b) can include titanium (+y) oxide (−x), e.g., titanium dioxide, and step (b) can include exposing the medical device to conditions sufficient to cause desired regions of the surface bearing titanium (+y) oxide (−x) to become hydrophobic or hydrophilic. The desired regions can be surfaces, e.g., abluminal, luminal and/or side wall surfaces, defining the depression. The desired regions can be surfaces, e.g., abluminal, luminal and/or side wall surfaces, that do not define the depression. The coating can be applied at a thickness about equal to the depth of the depression to which the coating is applied, e.g., about 50% to about 90% of the thickness of the band or connector that defines the depression. The coating can be applied at a thickness of less than the depth of the depression to which the coating is applied.

Following step (b), the coating can be removed from desired regions of the device, e.g., from surfaces exterior to the depression. The removal process can include grinding off the coating. The removal process can include rinsing off the coating.

In another aspect, the disclosure features a method of producing a medical device, including: (a) generating a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure, and wherein one or more wall surfaces bear a coating defining at least one depression; and (b) further applying at least one desired substance to the device.

Embodiments may include one or more of the following features.

The surface that bears the coating can be abluminal, luminal, side wall surface or a combination thereof.

The coating of step (a) can be applied by a sol-gel process. The process can include use of a nonsurfactant template, e.g., glucose or urea. The coating can include titanium (+y) oxide (−x), e.g., titanium dioxide. Between steps (a) and (b), the device can be exposed to conditions selected to cause the titanium (+y) oxide (−x) coating to become hydrophobic and/or hydrophilic, e.g., exposure to UV light (to cause the coating to become superhydrophilic) and/or long-term exposure to darkness (to cause the coating to become hydrophobic). The coating can define multiple depressions. The substance can be applied in step (b) preferentially to the depression. The substance applied in step (b) can be a biologically active substance. The substance applied in step (b) can be a polymer, e.g., a biodegradable polymer.

In another aspect, the disclosure features a method of producing a medical device, the method comprising: (a) generating a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure; (b) applying a first coating comprising a biologically active substance upon one or more surfaces of the medical device; and (c) applying a second coating to define at least one depression upon one or more surfaces of the medical device.

Embodiments can include one or more of the following features.

The first coating of step (b) can be applied to the abluminal wall surface, luminal wall surface, side wall surface or a combination thereof. The first coating can be applied by dipcoating, roll coating, MicroPen® application, electrospraying, gas-assisted spraying, electrospinning or a combination thereof. The first coating can include at least one biologically active substance, a polymer, e.g., a biodegradable polymer, a tie layer, e.g., a biodegradable tie layer, or a combination thereof.

The second coating of step (c) can be applied by a sol-gel method. The method can include using a nonsurfactant template, e.g., glucose or urea. The second coating can include titanium (+y) oxide (−x), e.g., titanium dioxide. Following application of the second coating comprising titanium (+y) oxide (−x), the device can be exposed to conditions selected to cause the titanium (+y) oxide (−x) coating to become hydrophobic and/or hydrophilic, e.g., exposure to UV light (to cause the coating to become superhydrophilic) and/or long-term exposure to darkness (to cause the coating to become hydrophobic). The second coating can be applied upon a region(s) of the medical device distinct from a region(s) upon which the first coating had been applied. The second coating can be applied upon the first coating, and the second coating can be configured to allow diffusion of the biological substance of the first coating through the second coating.

Between steps (a) and (b) the desired surface(s) of the medical device can be activated by, e.g., plasma treatment, ultraviolet light activation, electrical charging of desired regions of the device and texturizing. The activated surface(s) can include the abluminal wall surface, the luminal wall surface, the side wall surface or a combination thereof.

In another aspect, the disclosure features a medical device comprising a stent, having the form of an elongated tubular structure with an outer wall surface, side wall surface and an inner wall surface defining a central lumen or flow passageway, and one or more depressions defined by one or more surfaces of the stent containing a substance positioned, in use, for a delivery into a fluid flow passage of a living body.

The term "biologically active substance" as used herein refers to chemical compounds, therapeutic agents, drugs, pharmaceutical compositions and similar substances that exert biological effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the disclosure will be apparent from the following detailed description, and from the claims.

DESCRIPTION OF DRAWINGS

Like reference symbols in the various drawings indicate like elements.

DETAILED DESCRIPTION

Medical devices, such as endoprostheses or stents, often need to be delivered into a vessel of a living body with biologically active substances, e.g., drugs, that can subsequently be eluted from such devices. Medical devices are generally coated with such substances on their outer, or abluminal, surface. The substances can be embedded, e.g., in a soft, biodegradable, polymeric matrix coating. During delivery, e.g., via a catheter, however, the coating can be torn off due to shear forces. The coating can be stripped off as the stent is expelled from a catheter. For example, shear forces between a self-expanding stent and an enclosing delivery tube can cause damage to the coating of the stent, as the stent is being pushed outward, while the tube is being withdrawn, allowing the stent to expand. Coatings of balloon-expandable stents can also be damaged during passage of the devices through calcified lesions or through other devices used in stent procedures. Self-expanding and balloon-expandable stents are also prone to damage by shear forces generated as the stents expand and contact, e.g., walls of the target vessel. For example, expansion of a balloon-expandable stent inside a calcified lesion can damage stent coating. It would be advantageous to develop medical devices coated with biologically active substances that are protected during delivery of the device. This disclosure features such medical devices and methods of making such devices.

Figure 1A:
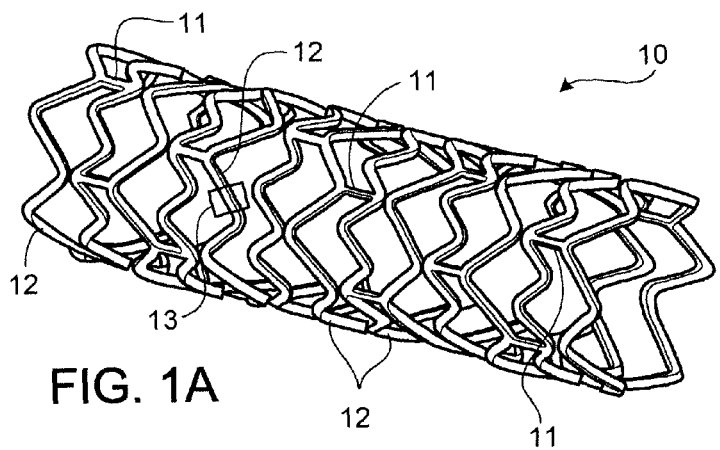
FIG. 1A is a perspective view of a stent.
Figures 1B, 1D, 1F:
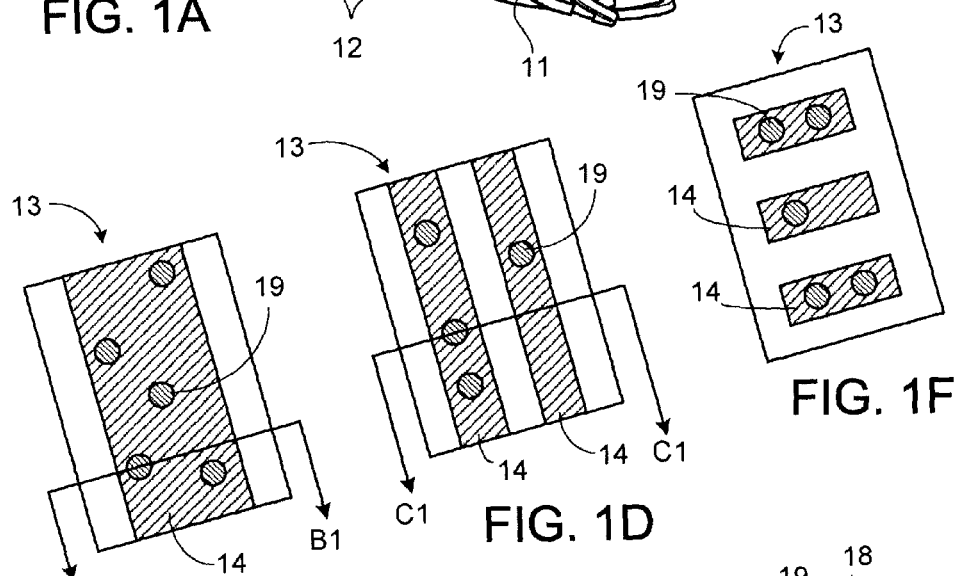
FIG. 1B is a top view of an embodiment of a section of a stent band.
FIG. 1D is a top view of an embodiment of a section of a stent band.
FIG. 1F is a top view of an embodiment of a section of a stent band.
Figure 1C:
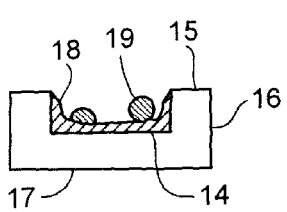
FIG. 1C is a cross-section of an embodiment of a stent band.
Figure 1E:
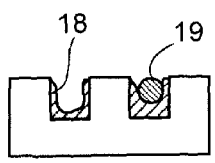
FIG. 1E is a cross-section of an embodiment of a stent band.
Figure 1G:
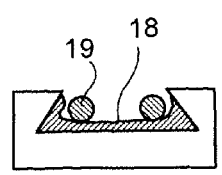
FIG. 1G is a cross-section of an embodiment of a stent band.

FIG. 1A shows stent 10 having a body of interconnected bands 12 and connectors 11 forming an elongated tubular structure. A top view of section 13 of one band 12 shown in FIG. 1B demonstrates that depression 14 extends generally along the axis of the band. Cross-section of section 13 taken along line B1-B1 is shown in FIG. 1C. The band has an abluminal (outer) wall surface 15, a side wall surface 16 and a luminal (inner) surface 17. Abluminal surface 15 bears a coating 18 defining depression 14. Coating 18 can include a polymer, e.g., a biodegradable polymer. The coating also includes a biologically active substance 19. Depression 14 can also extend generally along the axis of any of the connectors 11 (not shown). Depression 14 can extend generally in parallel to the axis of any of the bands 12 or connectors 11 (not shown). FIG. 1D and FIG. 1E show that multiple depressions 14 can be defined by coating 18 and extend generally along the axis of the band. Multiple depressions 14 can also extend generally in traverse, e.g., perpendicularly, to the axis of the band, as shown in FIG. 1F. The shape of the depression 14 can vary from the one shown in FIG. 1C and FIG. 1E. For example, the shape can include angles other than 90°, as shown in FIG. 1G, which is a cross section of band 12, taken along line B1-B1 of FIG. 1B. Undercutting sides of the depression shown in the embodiment of FIG. 1G, can further facilitate mechanical retention of the coating applied to the stent.

Depression 14 can constitute up to about 80% of the width of the band or the connector in which it is defined. The depth of depression 14 can constitute on average up to about 50% of the thickness of the band or the connector in which the depression is defined, but local depressions (analogous to potholes) can also constitute up to about 90% of the thickness of the band or connector.

Figure 2A:
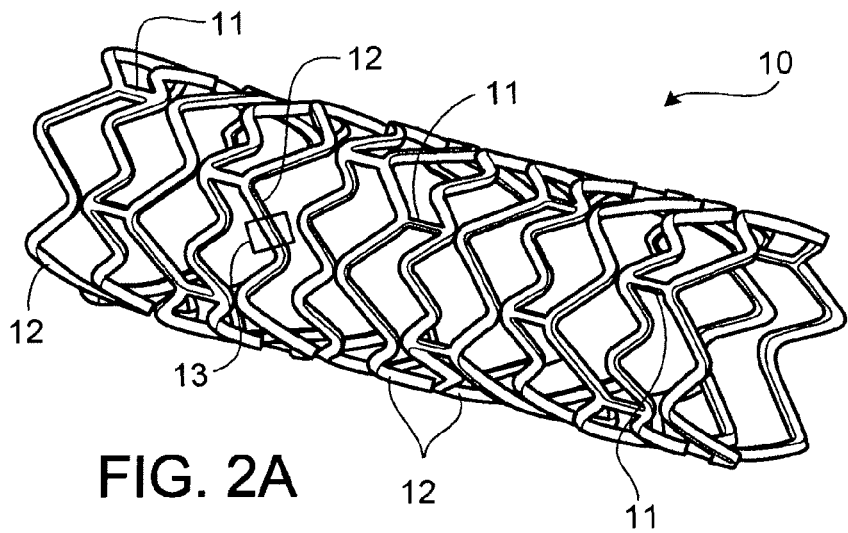
FIG. 2A is a perspective view of a stent.
Figure 2B:
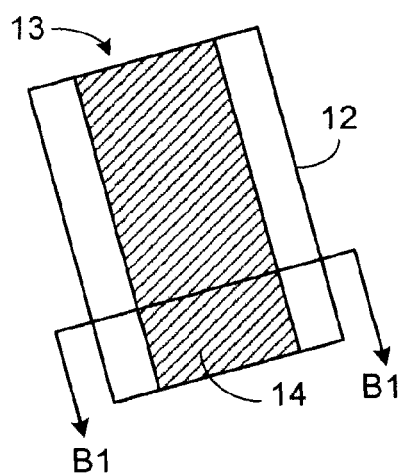
FIG. 2B is a top view of an embodiment of a section of a stent band.
Figure 2D:
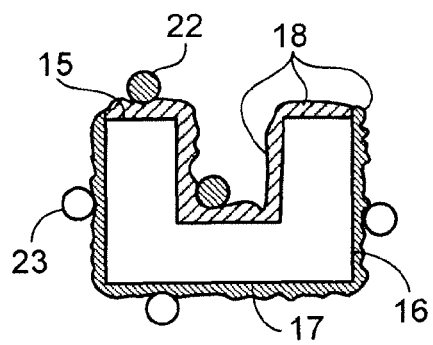
FIG. 2D is a cross section of an embodiment of a stent band.
Figure 2C:
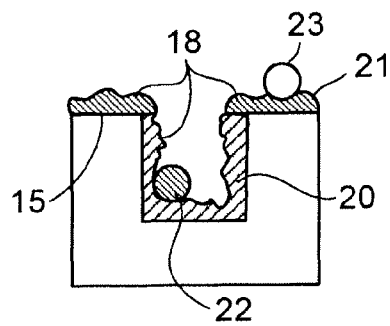
FIG. 2C is a cross section of an embodiment of stent band.

FIG. 2A through FIG. 2E show that various regions of the stent can bear depressions and various types of coating. FIG. 2A shows stent 10 having a body of interconnected bands 12 and connectors 11 forming an elongated tubular structure. In one embodiment, shown in FIG. 2B, depression 14 extends generally along the axis of band 12. FIG. 2C (which is a cross section of band 12 taken along line B1-B1 of FIG. 2B) shows that in one embodiment, coating 18 of the abluminal surface 15 can include a region 20 that defines depression 14 and a region 21 that does not define the depression. The properties of the coating in these two regions can vary, e.g., region 20 can include hydrophilic coating, e.g., hydrophilic titanium (+y) oxide (−x), e.g., hydrophilic titanium dioxide, e.g., superhydrophilic titanium dioxide, while region 21 can include hydrophobic coating, e.g., hydrophobic titanium (+y) oxide (−x), e.g., hydrophobic titanium dioxide (or vice versa). Such properties allow these regions to further include biologically active substances with different characteristics, e.g., a hydrophilic substance 22 in region 20 and a hydrophobic substance 23 in region 21.

Referring to FIG. 2D, in another embodiment, abluminal wall surface 15 includes coating 18 that defines depression 14, while the luminal and side wall surfaces 17 and 16, respectively, include coating 18 that does not define a depression. Again, the properties of coating of the abluminal surface and of the luminal and side surfaces can vary. For example, the coating of the abluminal surface can be hydrophilic, e.g., hydrophilic titanium (+y) oxide (−x), e.g., hydrophilic titanium dioxide, e.g., superhydrophilic titanium dioxide, while the coating of the luminal and side surfaces can be hydrophobic, e.g., hydrophobic titanium (+y) oxide (−x), e.g., hydrophobic titanium dioxide (or vice versa). These properties allow for the coating of the abluminal surface to include biologically active substances, e.g., hydrophilic substances 22, with properties differing from the biologically active substances of the luminal and side surface coating, e.g., hydrophobic substances 23.

Figure 2E:
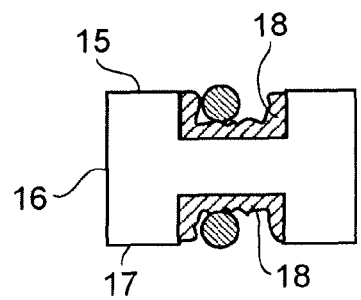
FIG. 2E is a cross-section of an embodiment of a stent band.

Referring to FIG. 2E, in yet another embodiment, the coating of both abluminal wall surface 15 and luminal surface 17 defines a depression. In another embodiment, the coating of side wall surface 16 can define a depression (not shown). The combinations of the regions of the coating that can define depressions are numerous. The combinations of the properties of various regions of the coating are also many.

As discussed above, coating 18 can include at least one releasable biologically active substance, e.g., a therapeutic agent, a drug, or a pharmaceutically active compound, such as described in U.S. Pat. No. 5,674,242, U.S. application Ser. No. 09/895,415, filed Jul. 2, 2001, and U.S. application Ser. No. 10/232,265, filed Aug. 30, 2002. The therapeutic agents, drugs, or pharmaceutically active compounds can include, for example, anti-proliferative agents, anti-thrombogenic agents, antioxidants, anti-inflammatory agents, immunosuppressive compounds, anesthetic agents, anti-coagulants, and antibiotics. Specific examples of such biomolecules include paclitaxel, sirolimus, everolimus, zotarolimus, picrolimus and dexamethasone. The coating can also include a polymer, e.g., a biodegradable polymer, that releases the biologically active substance as it degrades. Coating 18 can also include a tie layer that promotes its adhesion to the underlying stent 10. The tie layer can be biodegradable or non-biodegradable. Coating 18 can be a combination of biologically active substance(s), tie layer(s) and/or polymers. For example, the coating can include a layer of a first biologically active substance, and a layer of a polymer and a second biologically active substance (the first and second substances can be the same or different). The polymer can be biodegradable, exposing the first substance upon erosion. The polymer, e.g., a porous polymer, can allow the first substance to diffuse through and out of the polymer.

As discussed, coating 18 can include titanium (+y) oxide (−x) ($Ti_xO_y$) e.g., titanium dioxide ($TiO_2$). Titanium dioxide, also known as titanium (IV) oxide or titania is the naturally occurring oxide of titanium, chemical formula $TiO_2$. $TiO_2$ occurs in a number of forms: rutile, anatase, brookite, titanium dioxide (B) (monoclinic), titanium dioxide (II), and titanium dioxide (H). Carp et al., *Prog. Solid State Chem.* 32:33-177, 2004. One interesting property of $Ti_xO_y$, e.g., $TiO_2$, is that it can be either hydrophobic or hydrophilic, e.g., superhydrophilic. Stents coated with $Ti_xO_y$ and methods of coating stents with $Ti_xO_y$ are described in the U.S. Patent Application No. 60/818,101, filed Jun. 29, 2006, and U.S. patent application Ser. No. 11/763,770, filed on Jun. 15, 2007. As described therein, coating stent 10 with various combination of hydrophobic and/or hydrophilic $Ti_xO_y$ allows for placing various biologically active substances on selected regions of stent 10. The term "biomolecule" used in that application is equivalent to the term "biologically active substance" used herein.

Stent 10 can be used, e.g., delivered, using a catheter delivery system. Catheter systems are described, e.g., in Wang U.S. Pat. No. 5,195,969, Hamlin U.S. Pat. No. 5,270,086, and Raeder-Devens U.S. Pat. No. 6,726,712. Stents and stent delivery are also exemplified by the Radius® or Symbiot® systems, available from Boston Scientific Scimed, Maple Grove, Minn.

In use, stent 10, bearing at least one type of a biologically active substance, can deliver the substance to, e.g., a blood vessel. Biologically active substances can target various cells of the blood vessels, e.g., endothelial cells or smooth muscle cells. As discussed, currently available stents deliver biologically active substances, e.g., drugs, that are directly exposed to the delivery catheter and/or to the target vessel. During expulsion of the stent from the catheter, some of the biologically active substances and polymers that bear them can be torn off and thus lost before their delivery to a target. For example, shear forces between a self-expanding stent and an enclosing delivery tube can cause damage to the coating of the stent, as the stent is being pushed outward, while the tube is being withdrawn, allowing the stent to expand. Coating of balloon-expandable stents can also be damaged during passage of the devices through calcified lesions or through other devices used in stent procedures. Self-expanding and balloon-expandable stents are also prone to damage by shear forces generated as the stents expand and contact, e.g., walls of the target vessel. For example, expansion of a balloon-expandable stent inside a calcified lesion can damage stent coating.

The medical devices described herein, e.g., stents, protect biologically active substances, which are located in depressions defined by the coating of the stents. These protected substances are delivered to their targets and allowed to gradually elute from the stents, e.g., as the polymer portion of the coating biodegrades. Because the devices described herein can minimize loss of biologically active substances, relatively lower amounts of the substances need to be provided in the stent coating, and the coating itself can be thinner than currently used coatings. For example, some currently-used coatings are about 10 μm thick and loaded with about 8.8% by weight paclitaxel. Such coatings release only about 10% of available paclitaxel. The stents described herein can include coating as thin as 3 μm, containing biodegradable polymers, and having up to a 100% release rate of a biologically active substance, as such coating is now protected during delivery.

Stent 10 can be made by a variety of methods, e.g., by laser ablation process, laser-assisted chemical etching, or chemical etching. An example of one method is outlined in FIG. 3. In method 30, a medical device, e.g., stent 10 having a body of interconnected bands 12 and connectors 11 forming an elongated tubular structure, is generated (step 31). The stent has an inner luminal wall surface 17, a side wall surface 16 and an outer abluminal surface 15, as described above, e.g., in FIG. 1C. At least one depression 14 is generated in one or more of the surfaces of the stent (step 32). The depression can be generated by laser, e.g., ultra-short pulsed laser, e.g., a laser system delivering femtosecond pulses in the ultraviolet range (about 248 nm), e.g., short-pulse dye excimer hybrid laser delivering about 500-fs pulses at 248 nm. Bekesi et al., *Appl. Phys. A* 76:355-57, 2003. The depression can also be generated by a UV laser, e.g., 248 nm or 193 nm laser, having pulse length in the nanosecond range. The depression can be generated with an ultra-short laser having pulse length of sub pico, femto, or even attosecond length, operating at various wavelengths, e.g., visible, infrared, or near infrared. The depression can be generated by, e.g., laser ablation process, laser-assisted chemical etching, or chemical etching. For example, femtosecond lasers that can be used with the featured stents and methods are available from Del Mar Photonics, see, e.g., http://www.femtosecondsystems.com/products/category.php/1/.

In one embodiment, multiple depressions 14 can be generated in any band or connector of stent 10. The depression or depressions can be configured to extend generally along the axis of any band or connector in which the depression(s) is defined, e.g., generally in a parallel orientation to the axis. The depression or depressions can also be configured to extend generally in a traverse orientation, e.g., generally perpendicularly, to the axis of the band or connector in which the depression(s) is defined. The depression can be further undercut or etched, generating angles other than 90°, as shown in FIG. 1G. Undercutting the depressions in such configurations can facilitate mechanical retention of coating applied to the depressions. The depression(s) can constitute up to about 80% of the width of the band or connected in which the depression(s) is defined The depth of the depression(s) can constitute on average up to about 50% of the thickness of the band or connector in which the depression(s) is defined, but local depressions (analogous to potholes) can constitute up to about 90% of the thickness of the band or connector.

Figure 3:
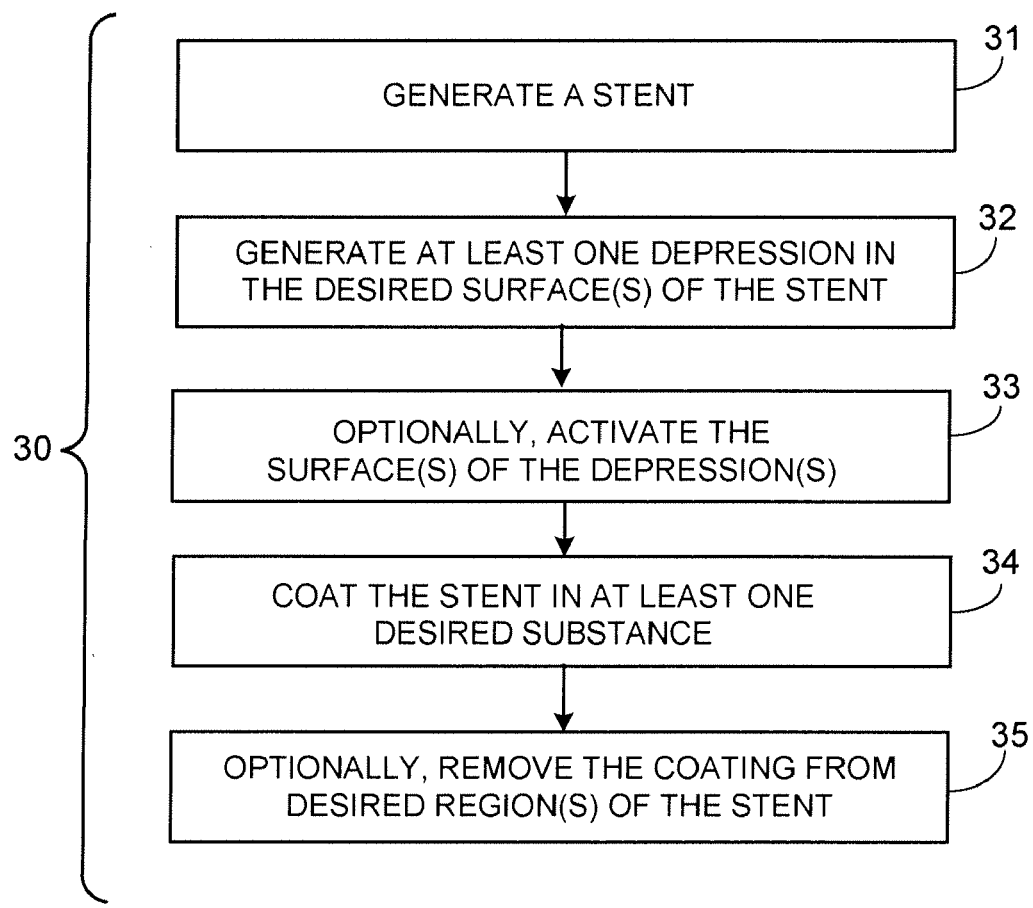
FIG. 3 is a flow chart of an embodiment of a method of making a stent.

Further referring to FIG. 3, after generating at least one depression, in some embodiments, the surface of the depression can be activated (step 33). The surface can be activated by, e.g., plasma treatment, texturizing and/or electrical charging the desired regions of the device. A coating including at least one desired substance is then applied to the stent (step 34). Activation of the surface in step 33 can increase adhesion of the coating in step 34. Applying the coating can be carried out by dipcoating, roll coating, MicroPen® application, electrospraying, gas-assisted spraying, electrospinning or a combination thereof. An example of applying a coating to a stent by electrospraying is described in, e.g., Weber et al. U.S. Pat. No. 6,861,088. Applying the coating can also be carried out by rolling the stent over a surface of a polymer tube that contains a biologically active substance. Such rolling directs or pushes the polymer and the substance into the depression(s) of the stent. The coating can also be applied by generating a rod of a polymer and a biologically active substance, e.g., a drug, which is inserted into a delivery device with a heated nozzle. The heated nozzle can be guided over the depressions and can melt the polymer/drug mixture as it expels and deposits the mixture into the depressions.

After the coating is applied in step 34, it may be localized to the surfaces inside the depression(s) and to the surfaces outside the depression(s). In one embodiment, it may be desirable to remove the coating from the surfaces outside the depression, leaving the coating mainly inside the depression (step 35). Removal of the coating from desired regions can be accomplished by grinding it off the desired surfaces or rinsing it off the desired surfaces.

The coating applied in step 34 can include $Ti_xO_y$, e.g., $TiO_2$. Following application of $Ti_xO_y$ coating, the medical device, e.g., a stent, can be exposed to conditions sufficient to cause desired regions of the device bearing $Ti_xO_y$ coating to become hydrophilic or hydrophobic. See, e.g., U.S. application Ser. No. 60/818,101, filed Jun. 29, 2006, and U.S. patent application Ser. No. 11,763,770, filed Jun. 15, 2007. The desired regions can include a surface that defines a depression, e.g., an abluminal, luminal and/or side wall surface that defines a depression. The desired regions can include a surface that does not define a depressions, e.g., an abluminal, luminal and/or side wall surface that does not define a depression.

The coating applied in step 34 can include at least one biologically active substance and/or a polymer. The biologically active substance can be hydrophobic or hydrophilic and preferentially bind to a hydrophobic or a hydrophilic coating, e.g., $Ti_xO_y$ coating described above. The coating can also include a tie layer to bind the coating to the underlying stent surface. The coating can include a combination of biologically active substance(s), polymers, and/or tie layer(s). For example, a coating of a first biologically active substance can be applied, followed by application of another layer of coating comprising a polymer and a second biologically active substance (the first and second substances can be the same or different). The polymer can be biodegradable, exposing the first substance upon erosion. The polymer, e.g., a porous polymer, can allow the first substance to diffuse through and out of the polymer.

Figure 4:
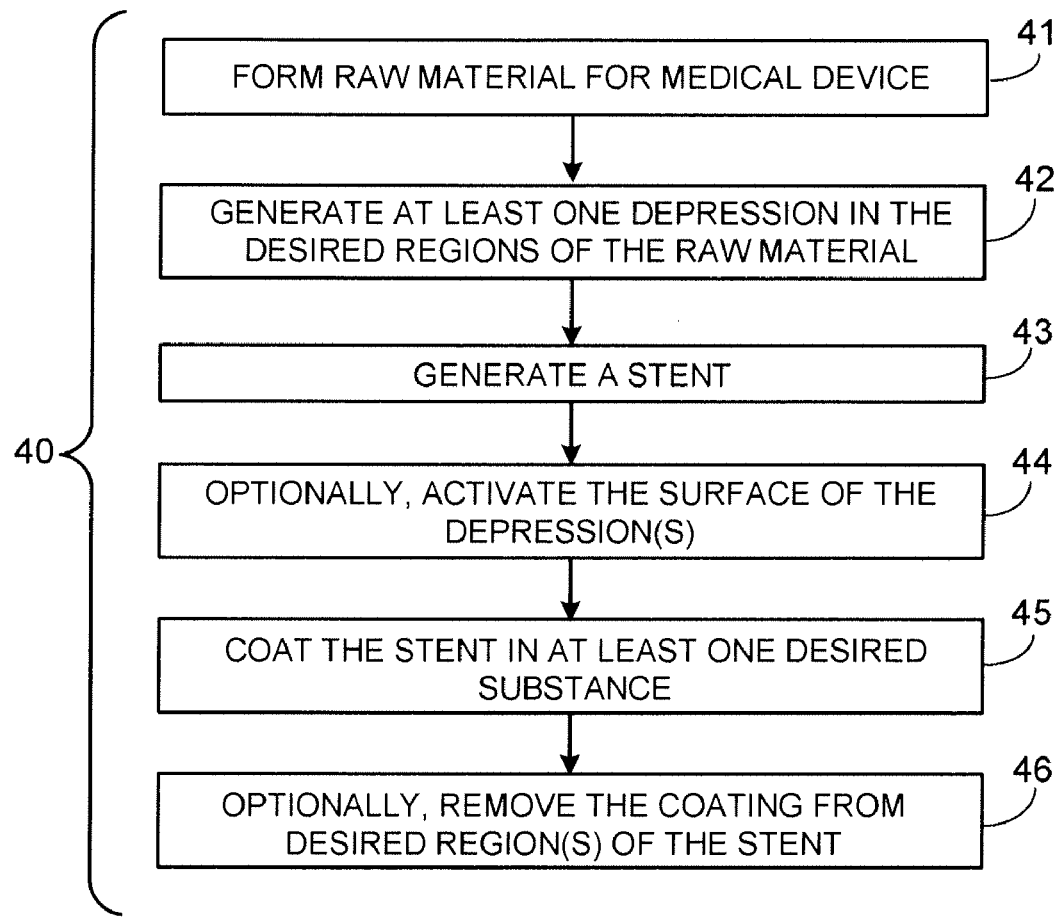
FIG. 4 is a flow chart of an embodiment of a method of making a stent.

Another example of generating the medical device is presented in FIG. 4. In method 40, raw material for a medical device is formed (step 41). The raw material can be, e.g., a tube. In step 42, at least one depression 14 is machined or formed into the desired region(s) of the raw material. In step 43, a stent is generated by, e.g., forming a pattern of bands and connectors into the raw material. The bands and connector define at least one depression 14. Steps 44-46 are analogous to steps 33-35 of FIG. 3 described above. Briefly, in step 44, the surface of the depression(s) can be, optionally, activated. The stent is coated in at least one desired substance (step 45). The coating can be, optionally, removed from desired region(s) of the stent (step 46).

Figure 5:
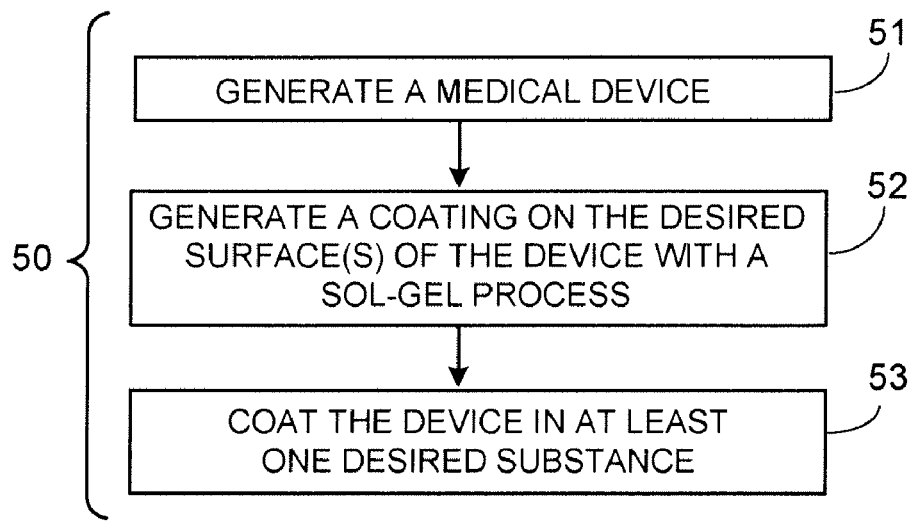
FIG. 5 is a flow chart of an embodiment of a method of making a stent.

Yet another example of generating the medical device is presented in FIG. 5. In method 50, a medical device, e.g., stent 10, is generated (step 51). Next, an in situ sol-gel process within a polyelectrolyte coating template is used to generate a coating upon the desired surface(s) of the stent (step 52). The coating is a ceramic coating bearing at least one depression, and preferably multiple depressions. The coating can be generated on abluminal, luminal and/or side wall surfaces of the device. The initial layer-by layer (LBL) self assembly polyelectrolyte coating can utilize various organic polyelectrolyte materials, e.g., polyacrylic acid (PAA), polycyclic aromatic hydrocarbons (PAH), polyethylene imide (PEI) and polystyrene sulfonate (PSS), deposited in a layer-by-layer method. In one embodiment, PEI is used as a first layer, followed by PAA/PAH or PSS/PAH layers. Macrosized polyelectrolyte materials, e.g., polystyrene, can be deposited in round ball-like structures or as fibers within this LBL structure. After the LBL coating has been deposited on the stent surface (or just within the depression) an in-situ sol-gel reaction is performed. The inorganic precursor in the process can be titanium-based, e.g., titanium (IV) bis(ammonium lactate) dihydroxide (TALH) or titanium (IV) butoxide (Ti(OBu)$_4$). Titanium oxide-based surfaces promote endothelial cell adhesion, which, in turn, may prevent thrombogenicity of stents delivered to blood vessels. Chen et al., *Surf. Coat. Tech.* 186:270-76, 2004. Within the in-situ sol-gel reaction, the precursor is mixed with an organic solvent, i.e. ethanol, and the sol-gel precursor therefore only hydrolizes within the polyelectrolyte layers by the presence of entrapped water molecules from previous steps. After the in situ sol-gel reaction, the organic template (polyelectrolyte materials) is removed by calcination at a high temperature. Removal of the organic template leaves depressions or pores in the overall structure where the organic template had been. In general, sol-gel-derived ceramic porous layers are generated with use of a surfactant (polymer) as a template, which needs to be removed at high temperatures. See, e.g., Cernigoj et al., Thin Solid Films 495:327-332, 2006. To avoid the use of high temperatures, in method 50, a nonsurfactant, e.g., glucose or urea, can be used to generate the ceramic layer. Zheng et al., *J. Sol-Gel Science and Tech.* 24:81-88, 2002. Glucose or urea can be removed with use of water at room temperature and leave behind a pure porous layer, e.g., nanoporous Titania layer. Changing template contents can generate materials with different pore sizes, thus allowing generation of a required drug release profile. For example, urea leaves larger pores than glucose. Because many nonsurfactants are biocompatible, they can also be allowed to remain in the sol-gel layer until they bioerode in the body after delivery of the stent.

Examples of sol-gel process are provided, e.g., in Maehara et al., *Thin Solid Films* 438-39:65-69, 2003; Kim et al., *Thin Solid Films* 499:83-89, 2003; and Bu et al., *J. Europ. Cer. Soc.* 25:673-79, 2005. To obtain selective coating, e.g., coating of the abluminal surface only, instead of using a layer-by-layer process within a solution, alternative layers of cationic and anionic molecules are micro-contact printed on the desired surface of the stent. One embodiment of depositing ceramic coating with depressions is described in an Example below.

Further referring to FIG. 5, the device is next coated in at least one desired substance (step 53). The substance can adhere to the depressions generated by the sol-gel process and be protected during delivery of the device, e.g., via a catheter. The substance is a biologically active substance and, optionally, includes a polymer. The substance can adhere to the surface of the depressions.

Figure 6:
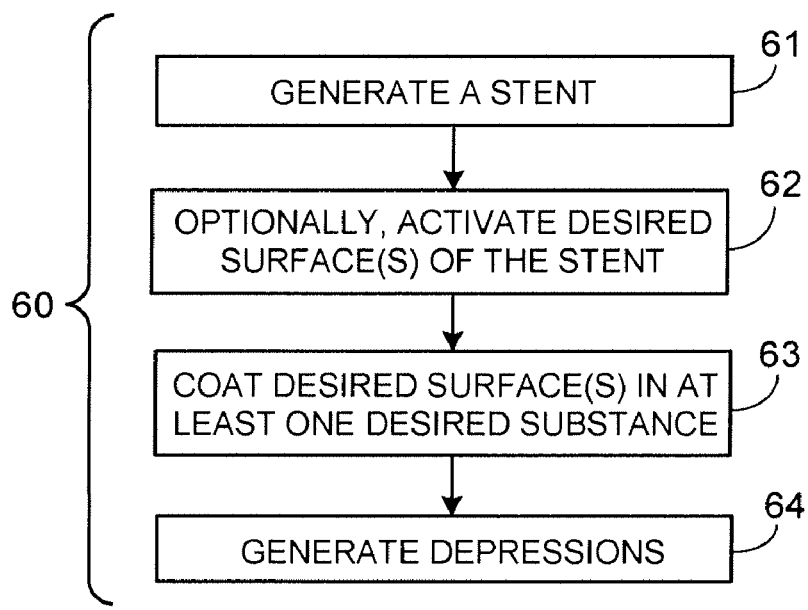
FIG. 6 is a flow chart of an embodiment of a method of making a stent.

Another example of generating a medical device is depicted in FIG. 6. In method 60, a stent is generated (step 61). Desired surface(s) of the stent can be optionally activated (step 62), as described above. Desired surface(s) of the stent can then be coated with desired substances, e.g., drugs and/or polymers as described supra (step 63). Hard walls can be deposited on at least one side of coated region(s), thereby generating depressions (step 64). The walls can be deposited by, e.g., a sol-gel process, e.g., by drawing a line on a desired surface(s), annealing and heat-treating to create hard walls. Steps 63 and 64 can be carried out simultaneously as one step. Alternatively, depressions can be generated in step 64 by applying a top layer of sol-gel derived, porous ceramic layer, e.g., nanonporous Titania or silica-Titania layer, onto the coating of step 63. As discussed supra, sol-gel-derived ceramic porous layers are often generated with use of a surfactant (polymer), which needs to be removed at high temperatures. See, e.g., Cernigoj et al. To avoid damaging the underlying biologically active substance, in method 60, a non-surfactant, e.g., glucose or urea, can be used to generate the ceramic layer. Zheng et al. Glucose or urea can be removed with use of water at room temperature and leave behind a pure porous layer, e.g., nanoporous Titania layer. The underlying biologically active substance can then diffuse through the top ceramic layer. The size of the pores in the ceramic layer can be adjusted (by changing template contents) to generate a required drug release profile. For example, urea leaves larger pores than glucose. In addition, because many nonsurfactants are biocompatible, they can also be allowed to remain in the sol-gel layer until they bioerode in the body after delivery of the stent.

Stent 10 can include (e.g., be manufactured from) metallic materials, such as stainless steel (e.g., 316 L, BioDur® 108 (UNS S29108), and 304 L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a super-elastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

In some embodiments, materials for manufacturing stent 10 include one or more materials that enhance visibility by MRI. Examples of MRI materials include non-ferrous metals (e.g., copper, silver, platinum, titanium, niobium, or gold) and non-ferrous metal-alloys containing superparamagnetic elements (e.g., dysprosium or gadolinium) such as terbium-dysprosium, dysprosium, and gadolinium. Alternatively or additionally, stent 10 can include one or more materials having low magnetic susceptibility to reduce magnetic susceptibility artifacts, which during imaging can interfere with imaging of tissue, e.g., adjacent to and/or surrounding the stent. Low magnetic susceptibility materials include those described above, such as tantalum, platinum, titanium, niobium, copper, and alloys containing these elements.

Stent 10 can be of a desired shape and size (e.g., coronary stents, aortic stents, peripheral vascular stents, gastrointestinal stents, urology stents, tracheal/bronchial stents, and neurology stents). Depending on the application, stent 10 can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 10 can be balloon-expandable, self-expandable, or a combination of both (e.g., U.S. Pat. No. 5,366,504).

While a number of embodiments have been described above, the invention is not so limited.

Figure 7:
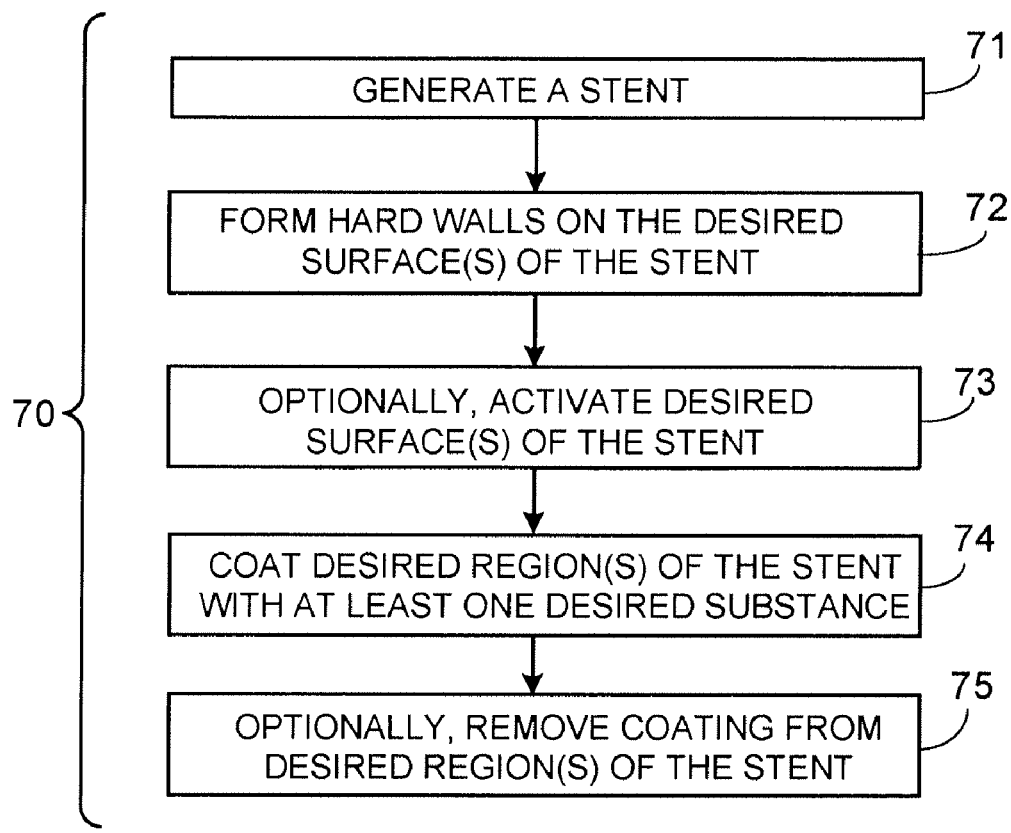
FIG. 7 is a flow chart of an embodiment of a method of making a stent.

For example, FIG. 7 depicts another method that can be utilized to generate a medical device. In method 70, a stent is generated (step 71). Next, hard walls are formed on the desired surface(s) of the stent, thereby generating depressions (step 72). The hard walls can be formed by, e.g., a sol-gel process, e.g., by drawing a line on a desired surface(s), annealing and heat-treating to create hard walls. The desired surface(s) of the stent can be optionally activated, as described above (step 73). Desired regions(s) of the stent, e.g., regions between the generated walls, can then be coated with desired substance(s), e.g., drugs and/or polymers as described above. Optionally, the coating can be removed from the desired region(s) of the stent (step 74).

In addition, various combinations of coating techniques can be used to generate medical devices whose surfaces define at least one depression. In one embodiment, stent 10 can first be coated in a desired non-conductive ceramic layer of a substance, e.g., $Ti_xO_y$, e.g. $TiO_2$. The coating can be carried out by a sol-gel process or conventional plasma immersion process. At least one depression can then be created by an ablating laser, e.g., femtosecond laser, in desired surfaces of the stent, exposing the underlying metal stent. In this embodiment, the metal regions of the stent define at least one depression. The resulting metal regions can then be charged and electrosprayed with desired substances, see, e.g., Weber et al., U.S. Pat. No. 6,861,088.

EXAMPLE

Generation of Hollow Ceramic Capsules on Stainless Steel

Figure 8:
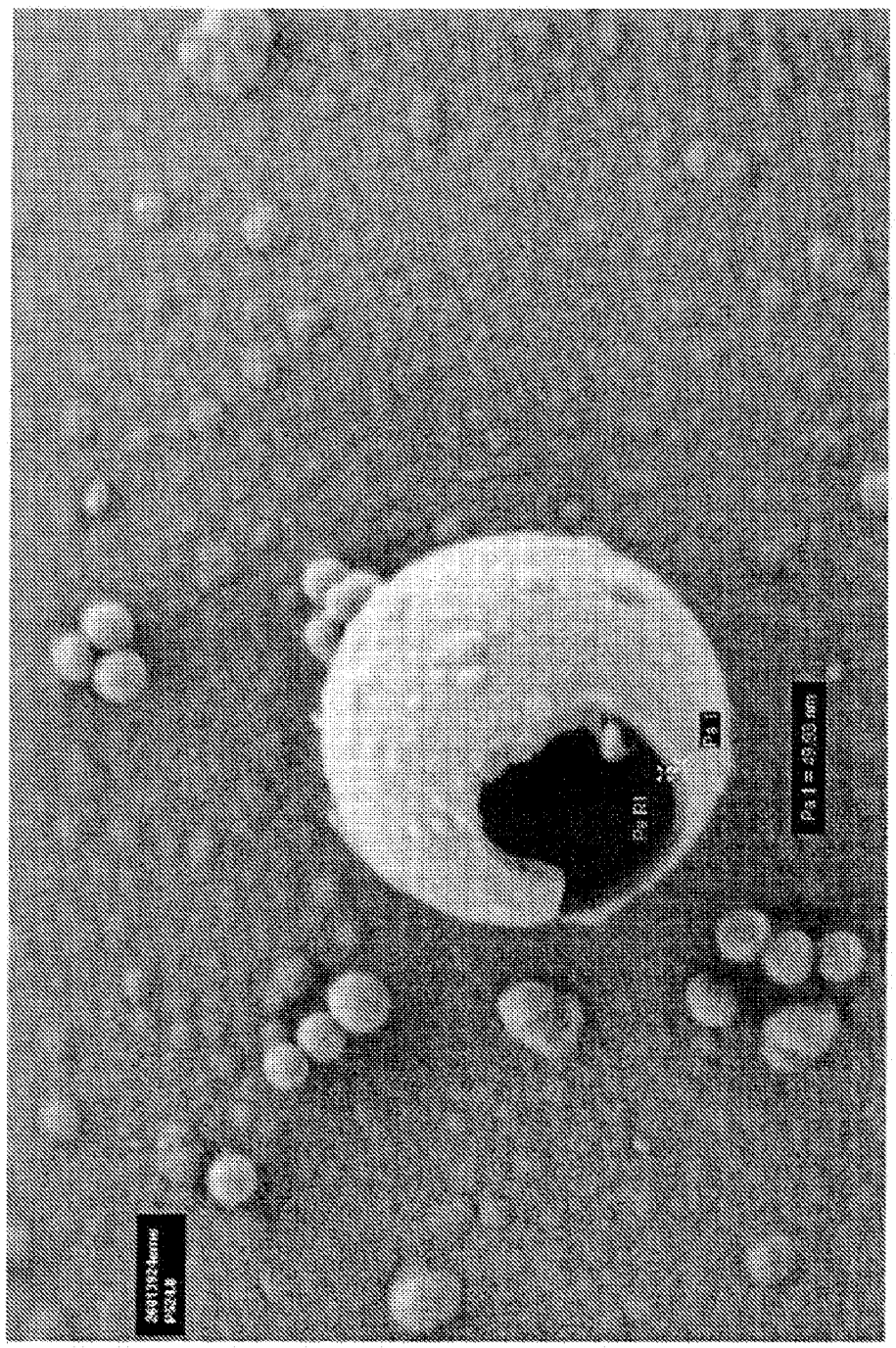
FIG. 8 is a scanning electron microscope image of a hollow ceramic sphere on top of steel.

As FIG. 8 shows, hollow ceramic (silica) capsules were generated on stainless steel. Anionic and cationic layers of poly-styrene-sulfonate (PSS) and poly-ethylene-imine (PEI), respectively, along with 1000 nanometer polystyrene balls (obtained from Microparticles\Forschungs- und Entwicklungslaboratorium, Volmerstr. 9A, UTZ, Geb.3.5.1, D-12489 Berlin) were deposited using a layer-by-layer process. Next, an in situ reaction of a sol-gel solution was carried out in pure ethanol with 15% water in the layers of tetraethyl orthosilicate (TEOS). The polyelectrolyte layers attract water because of their ionic charge, and their water content increases above 15%, thus activating the sol-gel reaction. This method is very controlled and stops automatically once the layers are saturated and charge density decreases. There is a direct correlation between the amount of polyelectrolyte layers and the depth of the final sol-gel layer. After the sol-gel layer was generated, the sol-gel and polystyrene construction was calcinated at 600° C. An example of the resulting 50 nm diameter hollow ceramic (silica) capsule is show in FIG. 8.

A number of embodiments have been described. Nevertheless, it will be understood that various modifications may be made without departing from the spirit and scope of the disclosure. Accordingly, other embodiments are within the scope of the following claims.

What is claimed is:

1. A medical device comprising:
   a body of interconnected bands and connectors forming an elongated tubular structure having an inner luminal wall surface, an outer abluminal wall surface and a side wall surface, and defining a central lumen or passageway,
   a coating on selected regions of one or more wall surfaces of the elongated tubular structure, the coating comprising a first region that defines a depression and a second region outside the depression, the coating in the first region being one of hydrophilic and hydrophobic and the coating in the second region being the other one of hydrophilic and hydrophobic.

2. The medical device of claim 1, wherein the coating is on the abluminal wall surface and defines the depression on the abluminal wall surface.

3. The medical device of claim 1, wherein the coating comprises at least one biologically active substance.

4. The medical device of claim 3, wherein the coating further comprises a polymer.

5. The medical device of claim 1, wherein the coating comprises a tie layer.

6. The medical device of claim 1, wherein the coating comprises a ceramic layer.

7. The medical device of claim 1, wherein the coating comprises titanium (+y) oxide (−x).

8. The medical device of claim 1, wherein the depression is configured to extend generally along the axis of the band or connector in which the depression is defined.

9. The medical device of claim 1, wherein the depression is configured to extend generally in a traverse orientation to the axis of the band or connector in which the depression is defined.

10. The medical device of claim 1 comprising multiple depressions defined in the selected regions of the coating of one or more wall surfaces.

11. The medical device of claim 1, wherein the width of the depression constitutes up to about 80% of the width of the band or the connector in which the depression is defined.

12. The medical device of claim 1, wherein the depth of the depression constitutes up to about 50% of the thickness of the band or the connector in which the depression is defined.

13. The medical device of claim 1, wherein the first region and the second region of the coating are both on the inner luminal wall surface or are both on the outer abluminal wall surface.

14. The medical device of claim 1, wherein the first region of the coating is on one of the inner luminal wall surface and the outer abluminal wall surface, and the second region of the coating is on the other one of the inner luminal wall surface and the outer abluminal wall surface.

15. A method of producing a medical device, the method comprising:
   (a) providing a medical device having a body of interconnected bands and connectors forming an elongated tubular structure having an inner luminal wall surface, an outer abluminal wall surface and a side wall surface, and defining a central lumen or passageway, wherein said inner luminal wall surface and side wall surface of the bands and connectors form transverse passageways through the elongated tubular structure; and
   (b) applying a coating upon selected regions of one or more surfaces of the elongated tubular structure, the coating comprising a first region that defines a depression and a second region outside the depression, the coating in the first region being one of hydrophilic and hydrophobic and the coating in the second region being the other one of hydrophilic and hydrophobic.

16. The method of claim 15, wherein the coating is applied on the abluminal surface and defines the depression on the abluminal surface.

17. The method of claim 15, comprising applying the coating of step (b) by a process selected from an array consisting of dipcoating, roll coating, MicroPen® application, electrospraying, gas-assisted spraying, and electrospinning, or a combination thereof.

18. The method of claim 15, comprising applying the coating of step (b) by rolling the medical device over the surface of a polymer tube comprising a biologically active substance to direct the polymer and the biologically active substance into the depressions of the medical device.

19. The method of claim 15, wherein step (b) further comprises activating the surface of the depression.

20. The method of claim 19, wherein the activating process is selected from the group consisting of plasma treatment, ultraviolet light activation, electrical charging of desired regions of the device and texturizing, or a combination thereof.

21. The method of claim 15, wherein the coating applied in step (b) comprises a biologically active substance.

22. The method of claim 21, wherein the coating further comprises a polymer.

23. The method of claim 15, wherein the coating applied in step (b) comprises a tie layer.

24. The method of claim 15, wherein the coating applied in step (b) comprises titanium (+y) oxide (−x).

25. The method of claim 24, wherein step (b) further comprises exposing the medical device to conditions sufficient to cause the first region or the second region of the coating comprising titanium (+y) oxide (−x) to become hydrophobic.

26. The method of claim 24, wherein step (b) further comprises exposing the medical device to conditions sufficient to cause the first region or the second region of the coating comprising titanium (+y) oxide (−x) to become hydrophilic.

27. The method of claim 15, comprising, following step (b), removing the coating from desired regions of the device.

28. The method of claim 27, wherein the desired regions include some portions of surfaces outside the depression.

29. The method of claim 15, further comprising, in step (a), generating at least one depression by laser in one or more surfaces of the body.

30. The method of claim 15, comprising applying the coating of step (b) by a sol-gel process.

31. The method of claim 15, wherein the coating defines multiple depressions.

32. The method of claim 15, further comprising applying a biologically active substance on one or more surfaces of the elongated tubular structure.

33. The method of claim 15, wherein the first region and the second region of the coating are both on the inner luminal wall surface or are both on the outer abluminal wall surface.

34. The method of claim 15, wherein the first region of the coating is on one of the inner luminal wall surface and the outer abluminal wall surface, and the second region of the coating is on the other one of the inner luminal wall surface and the outer abluminal wall surface.

* * * * *

UNITED STATES PATENT AND TRADEMARK OFFICE
CERTIFICATE OF CORRECTION

| | | Page 1 of 1 |
|---|---|---|
| PATENT NO. | : 8,353,949 B2 | |
| APPLICATION NO. | : 11/852475 | |
| DATED | : January 15, 2013 | |
| INVENTOR(S) | : Weber et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1439 days.

Signed and Sealed this
Ninth Day of June, 2015

Michelle K. Lee
*Director of the United States Patent and Trademark Office*